United States Patent
Tajima

(10) Patent No.: US 9,335,339 B2
(45) Date of Patent: May 10, 2016

(54) SPECIMEN TESTING DEVICE AND METHOD THEREOF

(75) Inventor: Hideji Tajima, Matsudo (JP)

(73) Assignee: UNIVERSAL BIO RESEARCH CO., LTD., Matsudo-Shi, Chiba (JP)

( * ) Notice: Subject to any disclaimer, the term of this patent is extended or adjusted under 35 U.S.C. 154(b) by 287 days.

(21) Appl. No.: 13/376,007

(22) PCT Filed: Jun. 4, 2010

(86) PCT No.: PCT/JP2010/059523
§ 371 (c)(1),
(2), (4) Date: Feb. 6, 2012

(87) PCT Pub. No.: WO2010/140680
PCT Pub. Date: Dec. 9, 2010

(65) Prior Publication Data
US 2012/0122231 A1    May 17, 2012

(30) Foreign Application Priority Data
Jun. 4, 2009    (JP) .................................. 2009-135340

(51) Int. Cl.
*G01N 21/00* (2006.01)
*G01N 35/02* (2006.01)
*G01N 35/04* (2006.01)

(52) U.S. Cl.
CPC ...... *G01N 35/026* (2013.01); *G01N 2035/0436* (2013.01)

(58) Field of Classification Search
None
See application file for complete search history.

(56) References Cited

U.S. PATENT DOCUMENTS

| 4,087,248 A * | 5/1978 | Miles ............................ 436/506 |
| 6,620,612 B1 | 9/2003 | Bertling |

(Continued)

FOREIGN PATENT DOCUMENTS

| JP | 04-346800 | 12/1992 |
| JP | 08-062224 | 3/1996 |

(Continued)

OTHER PUBLICATIONS

International Search Report, mailed Sep. 7, 2010, by the ISA/JP, in connection with PCT/JP2010/059523.

(Continued)

*Primary Examiner* — Robert Xu
(74) *Attorney, Agent, or Firm* — Haynes and Boone, LLP

(57) ABSTRACT

The present invention relates to a specimen testing device and method thereof, and it is an object of the present invention to provide a compact and reliable specimen testing device and method thereof. The specimen testing device includes one, two or more test cartridge containers which comprise a plurality of accommodation parts which accommodate or can accommodate a specimen and one, two or more reagent solutions or testing tools used for testing the specimen, and which visibly display specimen information for identifying or managing the specimen and test information showing test content; an automatic testing unit which is attached with or supports the testing tools and which causes a reaction of the specimen and the reagent solution accommodated in the test cartridge containers to obtain a predetermined optical state; an optical measurement unit which measures the optical state obtained by the automatic testing unit; and a digital camera which captures an image of content including the specimen information and the test information and displayed on the one, two or more test cartridge containers to obtain image data.

14 Claims, 14 Drawing Sheets

(56) References Cited

U.S. PATENT DOCUMENTS

| | | |
|---|---|---|
| 2002/0007054 A1 | 1/2002 | Sakurai et al. |
| 2002/0123156 A1 | 9/2002 | Tajima |
| 2002/0155616 A1 | 10/2002 | Hiramatsu et al. |
| 2003/0124738 A1 | 7/2003 | Crosby |
| 2007/0090190 A1* | 4/2007 | Kuromatsu et al. ........... 235/454 |
| 2009/0234025 A1* | 9/2009 | Strachan .................... 514/772.3 |

FOREIGN PATENT DOCUMENTS

| | | |
|---|---|---|
| JP | 08-211071 | 8/1996 |
| JP | 08-320274 | 12/1996 |
| JP | 10-004230 | 1/1998 |
| JP | 11-266864 | 10/1999 |
| JP | 2001-075480 | 3/2001 |
| JP | 2001-349896 | 12/2001 |

OTHER PUBLICATIONS

International Preliminary Report on Patentability, completed Sep. 12, 2011, by the IPEA/JP, in connection with PCT/JP2010/059523.

* cited by examiner ns made by these, verotoxin, *salmonella, campylobacter, Vibrio parahaemolyticus, Legionella*, anthrax, mycotoxin (aflatoxin), tubercle *bacillus*, MARSA, influenza, or foot-

SPECIMEN TESTING DEVICE AND METHOD THEREOF

CROSS REFERENCE

This application is a United States national phase application of co-pending international patent application number PCT/JP2010/059523, filed Jun. 4, 2010, which claims priority to Japanese patent application number 2009-135340, filed Jun. 4, 2009, the disclosures of which are incorporated herein by reference.

TECHNICAL FIELD

The present invention relates to a specimen testing device and method which can automatically conduct a test by adding one, two or more types of reagents to a specimen such as blood collected from patients, and quickly, easily and reliably perform testing to recording of test results.

BACKGROUND ART

In recent years, following increases in interests about contamination between humans and animals, an epidemic of new influenza, occurrence of other various infection diseases, occurrence of hospital infection, food safety and environmental contamination, there are increasing occasions that tests are demanded which are conducted by adding one, two or more types of reagents to block collected from human or animals, or a specimen collected from food, soil or polluted water. Particularly, there are increasing demands to use, for example, blood, body fluid, urine and cells collected from patients to confirm safety (infection disease in particular) upon clinical practice, at home, upon emergency or at a hospital.

To conduct this test, a specimen collected from, for example, humans is accommodated in a container, a label or the like in which, for example, a name, age and sex of a patient, a collecting date and a collecting site if the specimen is soil are written is pasted on the container, and a predetermined amount of a reagent is dispensed and transported to the specimen and incubated to cause a reaction. To associate the name of the patient and the like with test content, these are input by an operator to a computer as data or written on paper.

For test itself among these operations, an automated device which collectively processes multiple specimens is developed by the inventors of the present invention and is used (Patent Literatures 1 and 2).

CITATION LIST

Patent Literature

Patent Literature 1: Japanese Patent No. 3115501
Patent Literature 2: Japanese Patent No. 3630499

DISCLOSURE OF INVENTION

Problem to be Solved by the Invention

However, a series of operations of accommodating a collected specimen in a container, displaying the name of a patient and the like on the container, conducting a test, and inputting or writing test content such as the name of the patient and the test result as data or on paper are usually shared by a plurality of people, and there are concerns that the name of the patient and the like and test result are mixed up.

Further, to conduct a test of a patient upon emergency or at home, although the name is hand-written and displayed or a barcode is usually displayed to show test content, these cannot be visually identified, and therefore there is a concern that mistakes occur.

Further, in case of a device which collectively handles multiple specimens, the device scale is large and this device is installed, and therefore patients need to go to a facility equipped with this testing tool to have a test, and there is a concern that carrying these devices to fields at which specimens are collected is laborious.

The present invention is made to solve the above problems, and a first object of the present invention is to provide a specimen testing device and method which can conduct reliably tests without medical errors such as mixed-ups of specimens upon testing of a specimen collected from patients. A second object of the present invention is to provide a specimen testing device and method which can reduce the burden on the user by coherently performing measurement to recording of a test related to one specimen. A third object of the present invention is to provide a specimen testing device and method which are easily carried to a field at which specimens are collected, and which can quickly conduct tests.

Means to Solve the Problem

A first aspect of the invention is a specimen testing device which has: one, two or more test cartridge containers which have a plurality of accommodation parts which accommodate or can accommodate a specimen and one, two or more reagent solutions or testing tools used for testing the specimen, and which visibly display specimen information for identifying or managing the specimen and test information showing test content; an automatic testing unit which is attached with or supports the testing tools and which causes a reaction of the specimen and the reagent accommodated in the test cartridge containers to obtain a predetermined optical state; an optical measurement unit which measures the optical state obtained by the automatic testing unit; and a digital camera which captures an image of content including the specimen information and the test information and displayed on the one, two or more test cartridge containers to obtain image data.

Meanwhile, "specimen information" is information required to identify or manage a specimen, and information for identifying a specimen includes, for example, attributes of a specimen which is, for example, a patient, animal, food, soil or polluted water from which a specimen is collected, such as a name, age, sex and ID number of the patient, a location at which food is sold, a place at which soil is collected, and a collecting date, and the physicality of the collected specimen such as the type of blood, urine, feces, body fluid or cells of the patient, type of food, type of soil and type of polluted water. Information for managing a specimen includes, for example, a person who collects the specimen, collecting date, person in charge of testing the specimen, and test date of the specimen.

"Test information" is information showing content of a test conducted for a specimen, and can include test items such as tumor marker, hormone (thyroid hormone TSH $T_3$ and $T_4$), in-vivo inflammation (CRP), (respiratory or food) allergy, infectious diseases (for specifying *Staphylococcus aureus, Clostridium perfringens, Bacillus cereus* or *Vibrio cholerae*, enterotoxin or *Clostridium botulinum* which are toxins made by these, botulinum toxin or *Escherichia coli* which are toxins made by these, verotoxin, *salmonella, campylobacter, Vibrio parahaemolyticus, Legionella*, anthrax, mycotoxin (aflatoxin), tubercle *bacillus*, MARSA, influenza, or footand-mouth disease of domestic animals which are toxins made by these), autoimmune disease (connective tissue disease and DNA antibody), myocardial markers (BNP, ProBNP and troponin), biochemical reaction, blood types (A, B, O or Rh (+−) type), content of serum, various items of gene information (for determining, for example, SNPs and base sequence), gene diagnosis, other various types of protein information, the type of a reagent used for a test, a production lot number of a reagent, the standard curve of a reagent, the type and structure of testing equipment, or the type of biological material fixed to carriers. These pieces of information are displayed by hand-writing, printing, a barcode or a QR (registered trademark) code (matrix type two-dimensional code).

"Digital camera" is used, so that captured image data can be easily taken in a memory of a computer using, for example, a USB cord. Consequently, the operator does not need to input these pieces of information using a keyboard of the computer. Further, this data can be easily transmitted, processed, copied and applied in various cases. For example, the image data may be transmitted by providing a communication unit in the specimen testing device.

The digital camera captures as one image, for example, the information displayed on the visible recording medium once at one image capturing position fixed to the medium, or is provided to move relatively with respect to the medium to capture images of the medium at one or a plurality of predetermined image capturing positions. In the latter case, when images are captured a plurality of times at image capturing positions, a combination of a plurality of images corresponds to content of one visible recording medium.

"Test cartridge container" is a container which has a plurality of accommodation parts which accommodate or can accommodate at least one reagent solution or testing tool, and one test cartridge container has a number of accommodation parts required to finish one test processing of one specimen or finish test processing in combination with another test cartridge container. The accommodation part has a well for temperature control, well for a specimen, well for a reagent, well for reaction and testing tool accommodation part. When the number of accommodation parts is three or more, the accommodation parts are preferably aligned in one row. When a reagent solution or the like is accommodated in the accommodation parts, the opening parts of the accommodation parts are covered by a piercable film to prevent evaporation, flow-out, drop and contamination.

"Testing tool" is attached to or supported by the automatic testing unit and obtains an optical state caused by a reaction, and includes, for example, a dispenser tip attached to the nozzle of the automatic testing unit of the dispenser and used, a piercing tip attached to the nozzle to pierce the film and used, a solid-phase built-in tip in which predetermined biological substances are fixed or can be fixed such that the predetermined biological substances are identified from an outside and which are attached to the nozzle and used, a PCR cap attached to the nozzle and moved, test carriers on which predetermined biological substances are fixed or can be fixed therein at a plurality of different positions such that the predetermined biological substances can be identified and which are supported by the automatic testing unit and used, or test paper supported and used by the automatic testing unit and a cap pressing rod-shaped working tool attached to the automatic testing unit and used.

"One, two or more test cartridge containers" are used, and therefore the number of test cartridge container is by no means limited to one, and one specimen is tested by combining two or more test cartridge containers or two or more tests of specimens are processed in parallel. When two or more tests of specimens are processed in parallel, the two or more automatic testing units are provided. In addition, when the number of test cartridge containers is two or more, the test cartridge containers are aligned in the same row (alignment along the moving route direction of one automatic testing unit or longitudinal direction of the cartridge containers) for identical specimens, and the test cartridge containers are arranged in a different row for different specimens. In this case, the test cartridge containers in the same row have common specimen information. In addition, when the specimen testing device executes one test, all test cartridge containers aligned in one specimen testing device have common test information.

The "optical state" refers to, for example, presence/absence and measure of luminescence, light variation, color development or color change. The "automatic testing unit" obtains an optical state using the testing tool, and can relatively move the testing tool attached to or supported by the automatic testing unit, between each accommodation unit of the cartridge container.

A second aspect of the invention is a specimen testing device in which the digital camera has: an analyzing unit which analyzes the obtained image data to obtain analyzed data; and a data synthesizing unit which synthesizes the image data and the analyzed data to output.

"Analyze" is directed to analyzing whether or not there is code data such as predetermined one-dimensional barcode data or two-dimensional barcode data, number data, hue or QR code data in image data, and, when this code data is specified, converting this code data into analyzed data matching the code data. "Analyzed data" is obtained by converting code data such as the one-dimensional barcode data, matches the code data, and includes letters, numbers, symbols or figures which the user can visually check and understand. Content of analyzed data is, for example, the specimen information, test information or part of these pieces of information.

A third aspect of the invention is a specimen testing device in which the test cartridge container has: a visible recording medium which displays or can display the specimen information and the test information; and a medium attachment part to which the visible recording medium is attached, and further has a writing mechanism which automatically writes a measurement result of the optical measurement unit in an empty area of the visible recording medium.

"Visible recording medium" refers to a medium such as paper, thermal paper, resin or cloth on which information can be recorded, that is, printed or written to be identified by the eyes, has, for example, a sheet shape, plate shape, tape shape or film shape seal, and is arranged such that the information display face is oriented toward the digital camera so as to be captured by the digital camera.

A fourth aspect of the invention is a specimen testing device in which the writing mechanism has a thermal transfer printer mechanism which performs heating and printing to display a digital number.

A fifth aspect of the invention is a specimen testing device in which the visible recording medium is detachably attached to the medium attaching part of the test cartridge containers.

Meanwhile, "detachable attachment" means, for example, insertion in a transparent pocket or frame provided in the test cartridge container, pasting using an adhesive which can be peeled off, and attaching using a magic tape (registered trademark).

A six aspect of the invention is a specimen testing device in which: the automatic testing unit has a dispenser; the dispenser has: an suction/discharging mechanism which can suck and discharge gas; a nozzle which communicates with the suction/discharging mechanism and is detachably attached to the testing tools; and a moving mechanism which is provided with the nozzle relatively movably with respect to the test cartridge containers; and the testing tools are accommodated or can be accommodated in the test cartridge containers.

Meanwhile, "testing tool" attached to the nozzle has, for example, a tip shape which has a large diameter tube which has an attachment opening part which can be attached to the nozzle and a small diameter tube which communicates with the large diameter tube and has a size which allows its front end part to be inserted in the well, and is, for example, a dispenser tip which can suck and discharge a liquid by means of an suction/discharging mechanism, piercing tip and solid-phase built-in tip. The piercing tip has the large diameter tube having the attachment opening part, and has a sharply pointed front end part and can pierce the film, the solid-phase built-in tip is, for example, a carrier sealing tip in which carriers of specified or non-specified fixed positions are sealed or a fixed area sealing tip in which fixed areas of specified or non-specified fixed positions are sealed, and the carrier sealing tip has a tip shape which seals block or flat carriers in the large diameter tube, seals rod or wire carriers in the small diameter tube or large diameter tube or seals a plurality of particles in the small diameter tube.

Meanwhile, with carriers sealed in the carrier sealing tip in case where the fixed positions are specified or carriers used for the test carrier, chemical substances and the fixed positions of the chemical substrates such as particles of particle carriers are associated to be measured from an outside. The biological substances are chemical substances including biomacromolecules such as genetic substances such as nucleic acids, proteins, sugars, sugar chains or peptides, or low molecules and are used as ligands, to detect binding of, catch, separate and extract the biological substances which are receptors with the binding property for the biological substances of ligands. The receptors include biological substances such as genetic substances such as nucleic acids, proteins, sugar chains or peptides having the binding property with respect to biological substances such as genetic substances such as nucleic acids, proteins, sugar chains or peptides. Further, as biological substances or instead of biological substances, living organisms such as cells, viruses or plasmid can be used.

"Fix" is directed to binding and associating at least one type of the chemical substances with the carrier directly or indirectly through another type of a substance. Binding includes, for example, covalent binding, chemisorption, and, in addition, physisorption, hydrogen bonding and electric interaction. Further, "fix" also includes a specific reaction between binding substances of the particle carriers and various substances, and other methods. The size of "particle carriers" has the span or diameter of 0.1 mm to several mm.

Further, the fixed area sealing tip has a tip shape in which a fixed area which is fixed or can be fixed to a position such that predetermined biological substances can be identified from an outside is provided in an inner wall itself or is provided to be attached to an inner wall surface. These testing tools are accommodated in the accommodation parts of the test cartridge container with the attachment opening parts positioned at upper ends such that these testing tools can be attached when the nozzle is lowered.

In addition to a manual operation, by utilizing the moving mechanism of the dispenser as means for moving the test cartridge container to an outside from the housing in which the automatic testing unit and optical measurement unit are built in, it is possible to easily attach the test cartridge container to the specimen testing device.

A seventh aspect of the invention is a specimen testing device in which the test cartridge containers have one, two or more wells which accommodate in advance one, two or more reagents used to test the specimen, and which are sealed with a piercable film, and accommodate or can accommodate a piercing tip which is detachably attached to the nozzle of the dispenser and can pierce the film.

A eight aspect of the invention is a specimen testing device in which: the automatic testing unit has a magnetic member which can apply and remove a magnetic force to and from an inside of the dispenser tip from an outside of the dispenser tip; and at least one well of the test cartridge containers accommodates a magnetic particle suspension in which magnetic particles are suspended in a liquid.

According to the present invention, for example, target substances which are separated from a specimen using the magnetic member which can apply the magnetic field to the magnetic particles and dispenser tip are labeled by luminescent substances, and the magnetic particles to which the target substances are bound are sucked by the dispenser tip, then are attracted by applying the magnetic force to the inner wall of the small diameter tube of the dispenser tip by applying the magnetic force using the magnetic member and transferred, and at last are transferred to the well in which the substrate solution is accommodated and suspended to cause chemiluminescence and test whether or not there are target substances by measuring luminescence.

A ninth aspect of the invention is a specimen testing device in which the automatic testing unit has a temperature controller which can control a temperature in at least one well of the test cartridge containers.

Meanwhile, "temperature control" is performed according to a polymerase chain reaction (PCR) method of quickly and easily amplifying specific DNA fragments, and for constant temperature enzyme reaction etc. The PCR method is directed to designing two complementary primers in template DNA, and replicating the area sandwiched by these primers in vitro. The method is directed to a PCR product by repeating a temperature cycle of incubating a reaction solution including template DNA, primer, nucleotide and heat-stable DNA polymerase at various temperatures and exponentially amplifying DNA.

One cycle includes incubating a container which accommodates a template DNA, primers, DNA polymerase, nucleotide and reaction buffer solution, under respective temperature conditions (at 94° C., 50° C. to 60° C. and 74° C.) at which two strands of DNA are denatured to one strand, the primers are annealed to one strand of DNA, the complementary DNA strand is synthesized with one strand, and the DNA fragment of one molecule is divided into two molecules. In the next cycle, the DNA fragment synthesized in the previous cycle becomes a template, and therefore the DNA fragments synthesized after n cycles are $2^n$ molecules.

"Temperature control" is directed to repeatedly maintaining one, two or more predetermined set temperatures of a target liquid or container at a determined number of times for a set time according to a set order. The command is given to the temperature controller by transmitting a corresponding signal based on a program.

"Predetermined temperature" is a target temperature at which a product such as a target liquid needs to reach, and, when nucleic acid such as DNA or oligonucleotide etc. contained in the liquid is amplified by the PCR method, is, for example, each temperature of about 94° C. and the temperature between 50° C. and 60° C. such as about 50° C. and about 72° C. required for a temperature cycle performed in the PCR method, that is, for denaturing, annealing, hybridizing or stretching DNA. Further, the predetermined temperature includes, for example, a transition promoting temperature which, when a predetermined high temperature transitions to a predetermine low temperature, cooling is performed at a transition promoting temperature lower than these predetermined temperatures and, when a predetermined low temperature transitions to a predetermined high temperature, heating is performed at a transition promoting temperature higher than these predetermined temperatures to shorten the transition time and settle one cycle time within a predetermined cycle time. "Predetermined time" refers to a time required to maintain each temperature and depends on a reagent, the liquid amount, the shape, material, size and thickness of the nozzle used in the PCR method, and is, for example, several seconds to several ten seconds in total in one cycle and is about several minutes to several ten minutes in the processing time of the overall PCR method. In addition, the predetermined time also includes the transition time.

A tenth aspect of the invention is a specimen testing device in which the automatic testing unit has: a cap which is openable with respect to an opening part of the well of which temperature is controlled; and a cap-blocked-duration functioning mechanism which uses the suction/discharging mechanism or the moving mechanism to enable the cap to be pressed, shaken or moved when the cap blocks the opening part.

"Using the suction/discharging mechanism or the moving mechanism" has been described, and therefore there are cases where, for example, the cap is pressed using the nozzle which is driven by the moving mechanism, the cap is pressed using a rod working tool which interlocks with the nozzle, or the cap is pressed using a rod working tool which interlocks with a piston which slides inside the cylinder which is driven by the suction/discharging mechanism.

The cap covers the opening part of the test cartridge container using the cap moving mechanism which relatively moves the cap with respect to the opening part, or covers the opening part by attaching the cap to the front end of the nozzle or rod working tool using the suction/discharging mechanism or moving mechanism and moving the nozzle or working tool to the opening part.

An eleventh aspect of the invention is a specimen testing device in which: the temperature controller has: a block which is provided with a translucent well accommodation hole in which the well is accommodated; and a heating/cooling unit which heats or cools the block; and the optical measurement unit can optically measure the interior of the well through the well accommodation hole of the block. Hence, for example, the ends of optical fibers of the optical measurement unit are provided in the well accommodation hole. An example of the well accommodation hole is a fitting hole which fits to the well, and the ends of the optical fibers are provided in, for example, the bottom of the fitting hole.

A twelfth aspect of the invention is a specimen testing device which further has an optical measurement rod which can be moved by the suction/discharging mechanism or a moving mechanism, and in which: the cap has translucency and is provided to fit to a front end of the optical measurement rod; and the optical measurement unit can optically measure an interior of the well through the cap by means of the optical measurement rod. Hence, for example, the ends of the optical fibers provided in the optical measurement unit are provided in the optical measurement rod to pass the cap and enable measurement of luminescence in the well.

In this case, there is a concern that the cap contacts the specimen, and therefore it is preferable to manage the cap together with the test cartridge by accommodating or enabling accommodation of the cap in the test cartridge container. In addition, the luminescence measurement rod is part of the optical measurement unit or is optically connected with the optical measurement unit. In addition, the cap preferably fits with, for example, a rod of the cap-blocked-duration functioning mechanism such as the nozzle in addition to the optical measurement rod.

A thirteenth aspect of the invention is a specimen testing device in which: in the test cartridge containers, a mineral oil or silicon oil is accommodated; and, in the well of which temperature is controlled, the mineral oil or the silicon oil is introduced.

Meanwhile, "mineral oil" refers to oil deriving from a crude petroleum oil, and "silicon oil" refers to an oil material containing molecules of a normal chain structure in which siloxane bond is 2000 or less. "Introduction" is performed by, for example, making the dispenser tip perform suction, moving or discharging.

A fourteenth aspect of the invention is a specimen testing device in which: the testing tools have a solid-phase built-in tip which can be attached to the nozzle and which are built in a state where a solid-phase can be measured from an outside; the test cartridge containers accommodate or can accommodate the solid-phase built-in tip; and the optical measurement unit which can optically measure an interior of the solid-phase built-in tip from an outside.

Meanwhile, optical measurement is performed by relative movement between the solid-phase built-in tip and light receiving end along an axial direction of the tip.

A fifteenth aspect of the invention is a specimen testing method which includes: visibly displaying specimen information for identifying or managing a specimen and test information showing test content, on one, two or more test cartridge containers which have a plurality of accommodation parts which accommodate the specimen and one, two or more reagent solutions or testing tools used to test the specimen; producing a predetermined optical state by causing a reaction of the specimen and the reagent solutions accommodated in the test cartridge containers, using the testing tools; measuring the optical state; and capturing an image of content including the specimen information and the test information and displayed on the test cartridge containers, by means of a digital camera to obtain image data.

A sixteenth aspect of the invention is a specimen testing method which further includes analyzing the image data and synthesizing the obtained analyzed data and the image data to output.

Effects of Invention

According to the first or fifth aspect of the invention, content including specimen information such as the name of patient for identifying or managing a specimen collected from the patient and test information showing test content and displayed on a test cartridge container is reliably and easily input to a data processing device which has a computer using a digital camera, content displayed on the test cartridge container such as specimen information and test information which is originally displayed on the test cartridge container to show a single association is reliably associated in data processing and input, so that it is possible to conduct a reliable test without medical errors such as mixed-ups of a specimen due to data input errors.

Further, by coherently performing measurement and recording automatically upon testing of one specimen, it is possible to reduce the burden of the user.

Further, by measuring the optical state upon testing of one specimen, it is possible to provide a device which has a structure which is simple, compact and easy to carry.

Further, content displayed on the test cartridge container such as the specimen information and test information can be automatically input in the memory of the computer, so that it is possible to reduce labor of inputting data and easily transition to processing such as processing and copying of the data.

According to the second or sixteenth aspect of the invention, even the specimen information and test information of various display formats such as hand-writing, printing or code data such as barcode data can be converted into data which can be read by people by way of analysis, so that it is possible to perform reliable processing by means of uniform display, and reduce the burden on the user when the user reads data.

According to the third aspect of the invention, by automatically displaying a measurement result on the test cartridge container, even the specimen information and test information are associated with the test result using the digital camera and obtained as image data, so that it is possible to conduct a reliable test without mixed-ups.

According to the fourth aspect of the invention, by displaying the test result using digital numbers, it is possible to form a compact and cheap device with a simple mechanism without expanding the device scale.

According to the fifth aspect of the invention, the visible recording medium is detachably attached to the test cartridge container, so that, by peeling only the visible recording medium off from the test cartridge container to use and copying the visible recording medium in addition to the output image data, data formats of two systems are obtained, thereby providing reliability.

According to the sixth aspect of the invention, by using the dispenser for the automatic testing unit and accommodating or enabling accommodation of the testing tool which is attached to or supported by the nozzle of the dispenser, in the test cartridge container, all components which contact the specimen can be managed as components of the test cartridge container, so that it is possible to reliably prevent cross-contamination of the specimen, thereby providing reliability and making management easier.

According to the seventh aspect of the invention, at least one, two or more reagent solutions are accommodated in each well of the test cartridge container and sealed by a film, the film is pierced and, consequently, the reagent solution is used, so that it is possible to reliably prevent cross-contamination and quickly perform processing.

According to the eighth aspect of the invention, by providing a magnetic member to a dispenser and accommodating a suspension of the magnetic particles in the test cartridge container, the magnetic particles bound with a target substance can be easily separated in the dispenser tip, so that it is possible to smoothly perform processing by moving the magnetic particles among the wells in order with holding the magnetic particles to the inside of the dispenser tip by means of the magnetic force.

According to the ninth aspect of the invention, a temperature controller is provided as the automatic testing unit for one well of the test cartridge container in addition to the dispenser. Consequently, upon incubation, it is possible to promote processing by performing processing at an optimal temperature, and amplify DNA using the PCR method which requires temperature control.

According to the tenth aspect of the invention, the cap which can block the opening part of the well using the moving mechanism of the dispenser, is provided to be pressed and, consequently, the well can be reliably sealed by the nozzle during temperature control, so that it is possible to add a temperature evenly to a PCR solution in the well, and reliably prevent contamination. Consequently, it is possible to reliably perform PCR processing for the specimen.

Further, the device according to the present invention can remove dew condensation produced upon temperature control and attached to the cap by shaking the cap by means of the nozzle of the dispenser, and reliably open and close the cap. Consequently, the device according to the present invention is suitable for a test of specifying base sequences of genes mainly using real time PCR.

According to the eleventh aspect of the invention, by optically measuring the interior of the translucent well through the well accommodation hole of the block of the temperature controller, it is possible to reliably perform optical measurement upon temperature control.

According to the twelfth aspect of the invention, optical measurement can be performed through the cap which blocks the opening part of the well of which temperature is controlled, and optical measurement is performed upon temperature control, at a point different from a point at which the temperature controller is provided, so that it is not necessary to change the structure of the temperature controller to perform optical measurement and reliably control the temperature and optical measurement without preventing temperature control.

Further, according to the sixth to ninth aspect of the inventions, various containers and various tips which are likely to contact a specimen used for a test are collectively formed in one test cartridge container, all reagents required for the test are accommodated in advance in the test cartridge container and are sealed by a piercable film, and the specimen information and test information related to the specimen and test are displayed, so that, by switching between units of the test cartridge containers, it is possible to easily utilize again, for example, the nozzle and optical measurement unit other than the test cartridge container, prevent cross-contamination, easily and reliably manage the specimen and test and provide high cost performance.

According to the thirteenth aspect of the invention, when the temperature of a liquid of a temperature control target is controlled, an oil film can be formed to prevent evaporation of the liquid, so that it is possible to prevent dew condensation on the cap, easily open and close the cap, reliably perform optical measurement, prevent gas from being contained in the liquid and perform uniform temperature control. Further, when mineral oil or silicon oil is used, the cap itself is not required and air does not enter between the oil film and liquid, so that the mechanism of sealing between the liquid and oil film during temperature control is not required. Further, dew condensation does not occur between the oil film and liquid, so that it is not necessary to, for example, shake the oil film and it is possible to simplify the structure.

According to the fourteenth aspect of the invention, the dispenser is used as the automatic testing unit, and the solid-phase built-in tip which has a built-in solid-phase such as carriers is attached to the nozzle of the dispenser to perform processing, so that, by, for example, providing a plurality of types of binding substances which can be bound with a target substance which is assumed as the solid-phase of the solid-phase built-in tip, it is possible to reliably specify or catch the assumed target substance.

DESCRIPTION OF THE EMBODIMENTS

Figure 1:
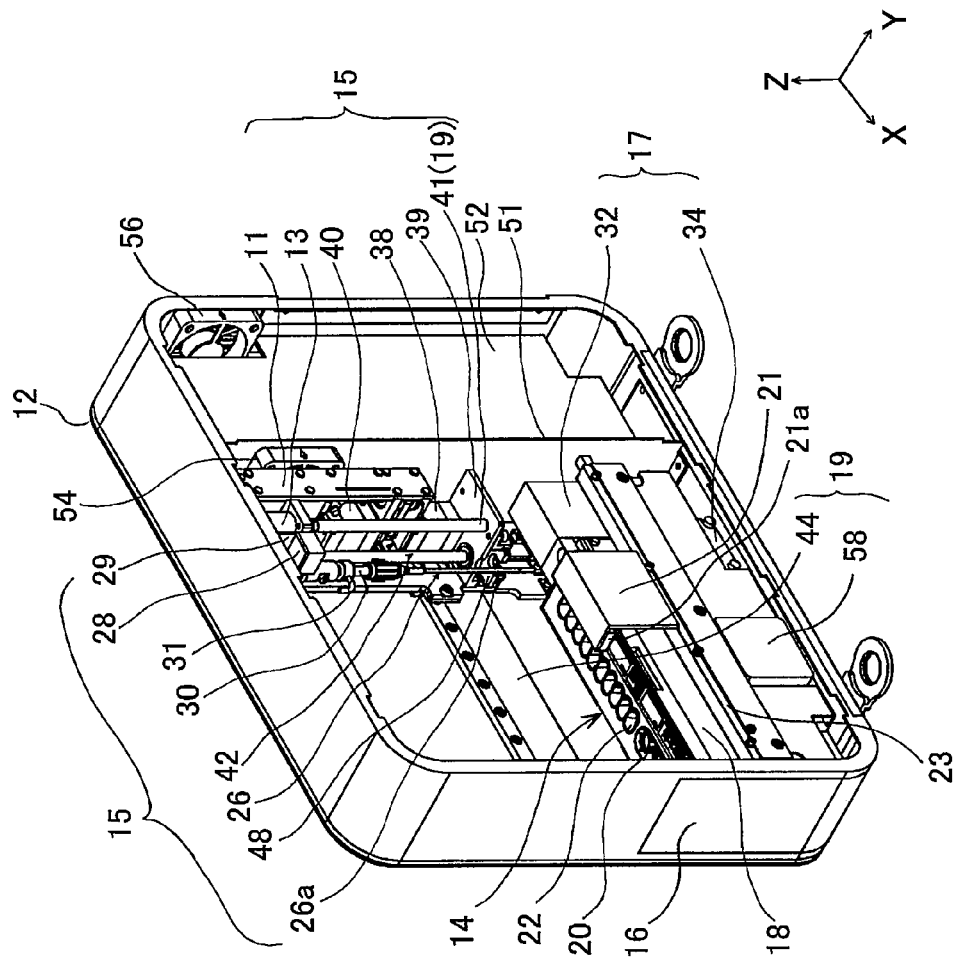
FIG. 1 is a perspective view where a part of a housing of a specimen testing device according to a first embodiment of the present invention is removed.

Next, a specimen testing device 10 according to a first embodiment of the present invention will be described based on FIGS. 1 to 6.

The specimen testing device 10 is surrounded by a book-shaped housing 12 of, for example, 250 to 400 mm long (X axis direction), 70 to 100 mm wide (Y axis direction) and 300 to 500 mm high (Z axis direction). The housing 12 has: a test cartridge container 14 in which a plurality of (ten with this example) wells 22 which accommodate or can accommodate a specimen and one, two or more reagent solutions used to test the specimen, and a tip accommodation part 20 which accommodates a plurality of types (three types with this example) tips of testing tools are aligned in one row and provided, which displays specimen information for identifying or managing the specimen and test information showing test content on a seal 24 of a visible recording medium, and which is formed with a translucent member; an automatic testing unit (15 and 19) which causes a reaction of the specimen and the reagents accommodated in the test cartridge container 14 to obtain luminescence in a predetermined optical state; an optical measurement unit 17 which measures the luminescence produced as a result of the test in the automatic testing unit; a digital camera 28 which captures an image of content displayed on the test cartridge container 14 including the specimen information and test information to obtain image data; a thermal transfer printer mechanism 21 which can print a test result on blank spaces of the seal 24 of the test cartridge container 14; and a board 52 which has an integrated circuit such as a CPU for controlling the automatic testing unit (15 and 19), the optical measurement unit 17, the digital camera 28 and the thermal transfer printer mechanism 21.

The test cartridge container 14 is detachably loaded to a loading box 18 which is jointed with a fitting plate 16, the fitting plate 16 is provided to be manually drawn forth to the outside of the housing 12 from the housing 12.

A chamber in which the automatic testing unit (15 and 19), test cartridge container 14 and optical measurement unit 17 are provided, and a chamber in which the board 52 is provided are partitioned by a partitioning plate 51 to prevent destruction and contamination of a circuit due to droplets of a liquid which are sucked and discharged. A ventilation fan 54 is provided to penetrate the partitioning plate 51, and another ventilation fan 56 is provided to penetrate the housing 12 of the chamber in which the board 52 is provided.

The automatic testing unit (15 and 19) has a nozzle head 15 of a dispenser, and a moving mechanism 19 which can move the nozzle head 15 with respect to the test cartridge container 14 accommodated in the housing 12.

The nozzle head 15 of the dispenser has: a X axis moving body 11 which can move in the X axis direction corresponding to a longitudinal direction with respect to the test cartridge container 14 accommodated in the housing 12 by means of the moving mechanism 19; and a Z axis moving body 13 which is movably provided to be guided by a guide column 41 in up and down directions with respect to the X axis moving body 11. To the X axis moving body 11, a nut part jointed to the Z axis moving body 13 is screwed and a Z axis moving ball screw 43 described later which moves the Z axis moving body 13 in the up and down directions is rotatably attached, and the guide column 41 and a support plate 39 which is attached through the guide column 41 are attached.

The nozzle head 15 has: a nozzle 30 which is attached to the Z axis moving body 13, in communication with a cylinder which sucks and discharges gas through an air rubber tube 31 which is provided to project from a lateral face; a motor 40 which drives a piston in the cylinder; and a ball screw 42 which is rotatably attached.

Further, the support plate 39 which is attached to the X axis moving body 11 rotatably supports the ball screw 42 and, beneath the support plate 39, supports movably in front and back directions a tip detaching plate 48 in which a U-shaped hole greater than the diameter of the nozzle 30 and smaller than the outer diameter of the thickest portion of the tip is formed to detach a tip such as a carrier sealing tip 26 from the nozzle 30 and, on the upper side of the support plate 39, a motor 38 which drives the tip detaching plate 48 in the front and back directions is attached to the X axis moving body 11.

The digital camera 28 is attached to the X axis moving body 11 through a camera support plate 29, and captures an image by moving the nozzle head 15 to a position at which the digital camera 28 can capture the entire specimen information and test information on the seal 24 of the test cartridge container 14 accommodated in the housing 12.

The moving mechanism 19 which moves the nozzle head 15 of the dispenser with respect to the test cartridge container 14 accommodated in the housing 12 has: a rail 44 which engages with and guides the X axis moving body 11 of the nozzle head 15 in the longitudinal direction, that is, the X axis direction of the cartridge container 14; a X axis moving motor 58 which moves the nozzle head 15 along the X axis direction; the guide column 41 which guides the Z axis moving body 13 in the up and down directions, that is, the Z axis direction; the Z axis moving ball screw 43; and a Z axis moving motor. In addition, the cylinder, the ball screw 42 and the motor 40 correspond to an suction/discharging mechanism. Further, the guide column 41, the Z axis moving ball screw 43 and the Z axis moving motor correspond to the Z axis moving mechanism in the moving mechanism 19.

The optical measurement unit 17 has: a tip inserting unit 34; and a photoelectric unit 32 which has at least one photoelectric element such as a photoelectric multiplier tube which converts received luminescence into a predetermined electric signal.

The thermal transfer printer mechanism 21 is connected with the optical measurement unit 17 through the board 52, receives an electric signal matching the measurement result of the optical measurement unit 17 and performs printing on the seal 24 of the test cartridge container 14. The thermal transfer printer mechanism 21 is preferably provided such that, when the test cartridge container 14 is inserted in the housing 12, the thermal transfer printer mechanism 21 is positioned above without contacting the test cartridge container 14, accommodates the test cartridge container 14 and is lowered by, for example, a cam mechanism, and a printer head 21a of the thermal transfer printer mechanism 21 is positioned in a predetermined blank portion on the seal 24 of the test cartridge container 14. The printer head 21a is directed to automatically writing digital numbers on the seal 24 formed with a heat sensitive medium by forming digital numbers of predetermined digits and heating a predetermined segment of the digital numbers of the printer head 21a.

Figure 2:
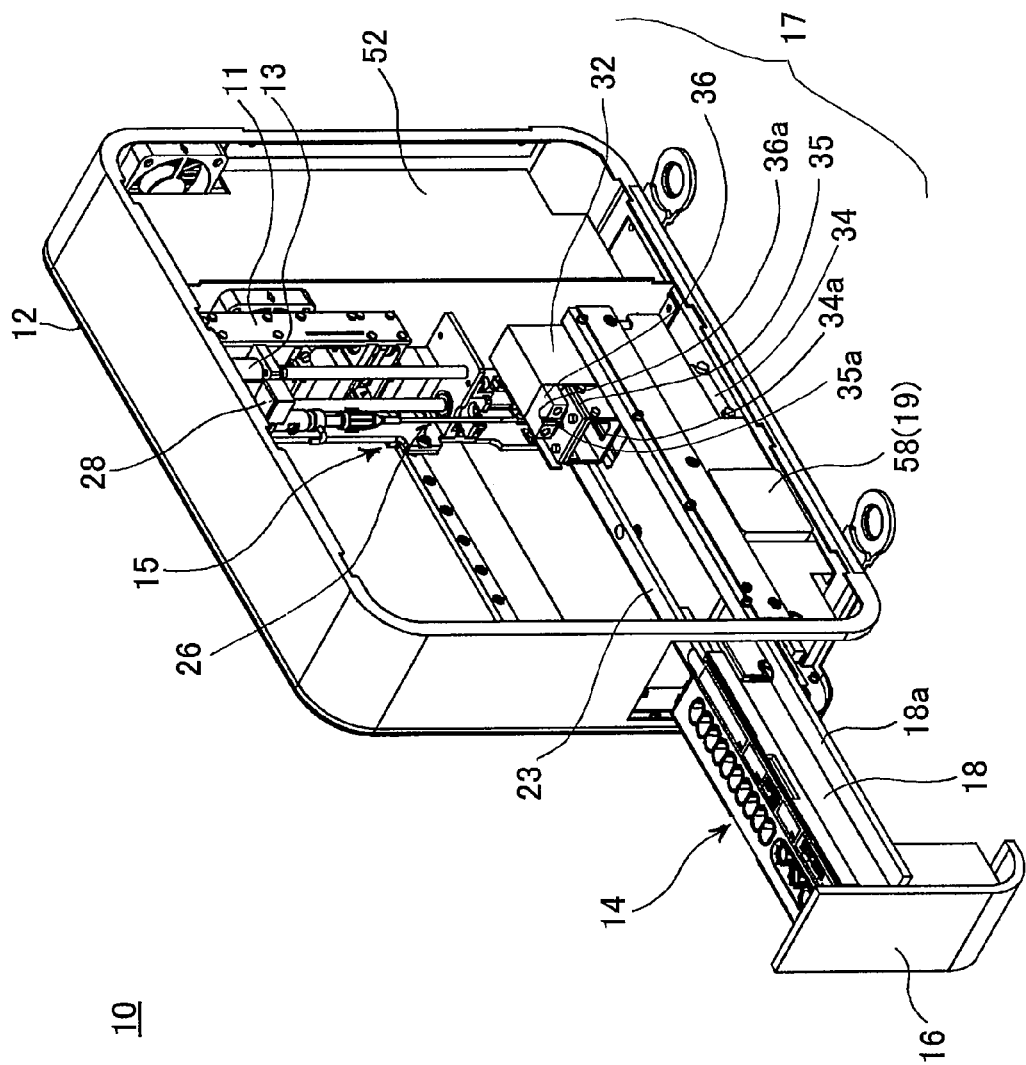
FIG. 2 is a perspective view where a part of components of the specimen testing device of FIG. 1 is removed and illustrates a state where a test cartridge container is drawn forth.

FIG. 2 illustrates a state where the test cartridge container 14 of the specimen testing device 10 is manually drawn forth from the housing 12. In addition, the thermal transfer printer mechanism 21 is removed for ease of description.

With the loading box 18 in which the test cartridge container 14 is loaded, a guide member 18a extending along the longitudinal direction of the loading box 18, that is, the X axis direction is provided to be guided by a guide rail 23 laid in the housing 12 along the X axis direction and manually moved in the X axis direction, so that it is possible to completely accommodate the test cartridge container 14 in the housing 12.

In addition, it is preferable to interlock insertion of the container 14 and upward and downward movement of the thermal printer mechanism 21 by providing the cam mechanisms in the guide member 18a and thermal transfer printer mechanism 21.

Further, a carrier sealing tip 26 in which particles 26c which are a plurality of carriers are accommodated is detachably attached to the nozzle 30 of the nozzle head 15.

The optical measurement unit 17 further has: a measurement block 36 at the rim of which a semi-circular hole 36a is formed and which is fixed to the photoelectric unit 32; and a measuring plate 35 at the rim of which an elongate hole 35a is formed below the measurement block 36 and above the tip insertion unit 34 and which is provided to be retreated back and forth along the longitudinal direction (X axis direction) of the elongate hole 35a by an electric magnet. The tip insertion unit 34 which is provided below the measurement plate 35 is formed in a box shape so that it enables a small diameter tube 26a of the carrier sealing tip 26 which is lowered passing through a cavity portion combined by the semi-circular hole 36a and elongate hole 35a to be inserted through a square hole 34a of the tip insertion unit 34. The measurement plate 35 and measurement block 36, and the photoelectric unit 32 are fixed to the housing 12 upon measurement, and scan and measure a plurality of particles 26c by raising and lowering the carrier sealing tip 26 with respect to the housing 12.

Figure 3:
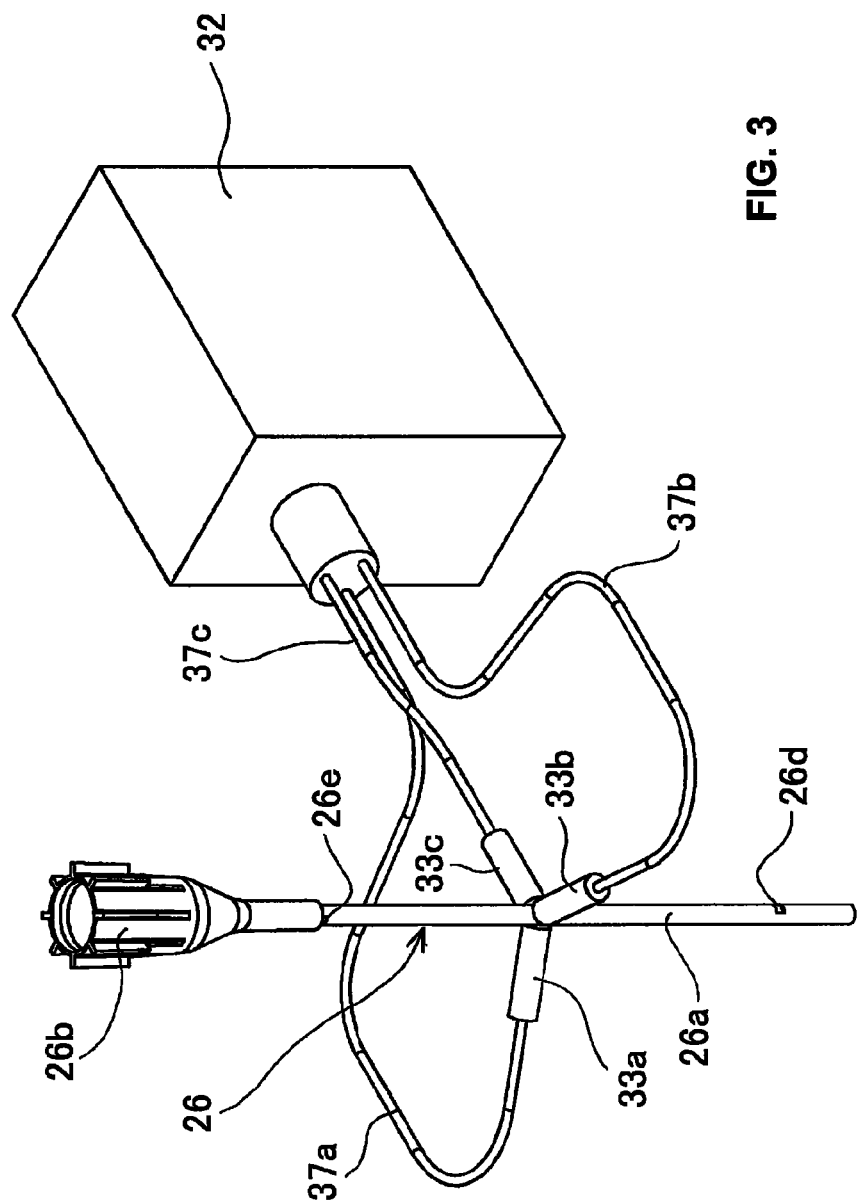
FIG. 3 is an enlarged perspective view of a component which is built in an optical measurement unit illustrated in FIGS. 1 and 2.

FIG. 3 is an optical system built in the optical measurement unit 17. The optical system is a device which is suitable to measure, for example, chemiluminescence, and has: three sets of optical fibers 37a, 37b and 37c; and light receiving ends 33, 33b and 33c provided at the front ends of the optical fibers and made of lenses. The light receiving ends 33a and 33b are arranged along a sidewall of the elongate hole 35a of the measurement plate 35, the light receiving end 33c is arranged in the sidewall of the semi-circular hole 36a of the measurement block 36, and these light receiving ends 33a, 33b and 33c surround the small diameter tube 26a of the carrier sealing tip 26 from three directions in a radial pattern. Upon insertion of the carrier sealing tip 26, the horizontal cross-sectional area of the cavity portion formed by the elongate hole 35a and semi-circular hole 36a is expanded by moving in a forward direction the measurement plate 35 using a magnetic force of the electric magnet, and, upon measurement, the horizontal cross-sectional area is narrowed by moving the measurement plate 35 in a backward direction and placing the measurement plate 35 close to the carrier sealing tip 26 inserted in the elongate hole 35a.

Figure 4:
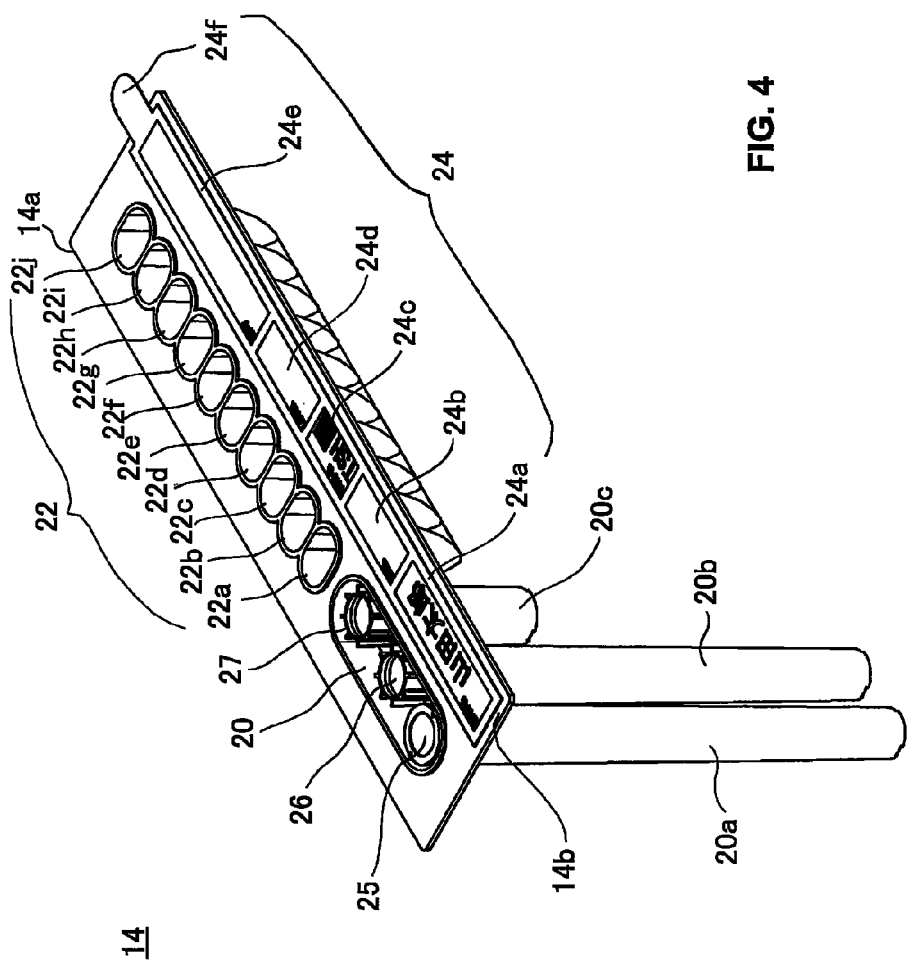
FIG. 4 is an enlarged perspective view of the test cartridge container illustrated in FIGS. 1 and 2.

FIG. 4 is a view enlarging the test cartridge container 14.

A base plate 14a of the test cartridge container 14 has an opening part of the tip accommodation part 20 and opening parts of the well 22. The volume of each well 22 is, for example, about 1 cc to several cc, and, for example, 2 cc. In the tip accommodation part 20, three tips with this example, that is, a dispenser tip 25, the carrier sealing tip 26 and a piercing tip 27 are accommodated in cylindrical bodies 20a, 20b and 20c having the corresponding depths with the attachment opening parts directed upward such that the dispenser tip 25, the carrier sealing tip 26 and the piercing tip 27 are attached when the nozzle 30 is lowered and inserted. In the ten wells 22, a specimen and one, two or more reagent solutions used to test the specimen are accommodated, and the opening parts are blocked by one film which can be pierced by the piercing tip 27. In addition, the opening part of the tip accommodation part 20 is blocked by the seal which can be manually peeled off, and are used by peeling off the seal upon use.

In a seal pasting area 14b which is the medium attaching part of the base plate 14a of the test cartridge container 14, the seal 24 which visibly displays specimen information (24a and 24b) and test information (24c, 24d and 24e) showing test content is detachably pasted. Meanwhile, for the test information (24a and 24b), for example, a space 24a in which the name of a patient is hand-written and displayed and a space 24b in which an identification number of the patient is displayed are provided, and, for test information (24c, 24d and 24e), a space 24c in which a test item is displayed, a LOT number space 24d in which a LOT number indicating management information such as a manufacturing place, a manufacturing period, expiration date, the number of manufactured reagents, storage location and quality of one, two or more reagents accommodated in advance in the test cartridge container 14, and a remarks space 24e in which a test result measured by the optical measurement unit 17 is written and displayed are provided. The test items include, for example, TSH (thyroid stimulation hormone), in-vivo inflammation and allergy tests, and are displayed by, for example, two-dimensional codes as illustrated in FIG. 3. In addition, 24f denotes a pick-up part for peeling off the seal 24 from the base plate 14a.

Figure 5:
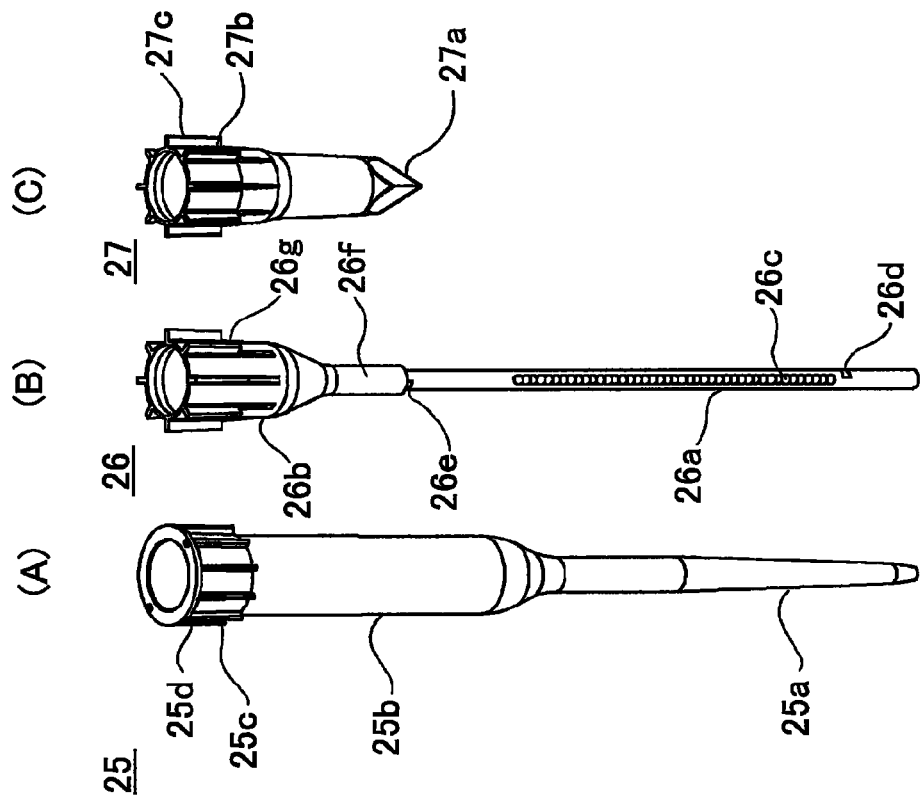
FIG. 5 is a perspective view illustrating various tips accommodated in the test cartridge container illustrated in FIG. 4.

FIG. 5 illustrates three types of tips (25, 26 and 27) accommodated in the tip accommodation part 20 of the test cartridge container 14.

As illustrated in FIG. 5(A), the dispenser tip 25 is used to suck a liquid to accommodate the liquid in a tip, discharge a liquid moved between the wells 22 and accommodated, and transport the liquid between the wells 22. The dispenser tip 25 has: a small diameter tube 25a which has the thickness which allows the front end to be inserted into the well 22; a large diameter tube 25b which communicates with the small diameter tube 25a and has at a rear end an attachment opening part to which the nozzle 30 can be attached; and a plurality of elongated protrusions 25d provided in parallel to the axial direction, at the rear end part of the large diameter tube 25b.

As illustrated in FIG. 5(B), with the carrier sealing tip 26, the particles 26c which are a plurality of (fourth three with this example) carriers are aligned in one row in the small diameter tube 26a having the thickness which can be inserted into the well 22, and each particle is fixed with binding substances to which target substances marked by fluorescence can be bound, and is sealed inside by calking the small diameter tube 26a at positions 26d and 26e. The small diameter tube 26a communicates with the large diameter tube 26b through a filter unit 26 provided with a filter which allows only air to pass, and the opening part of the large diameter tube 26b is provided to be attached to the nozzle 30. In the surrounding of the large diameter tube 26b, a plurality of elongated protrusions 26g are provided in parallel to the axial direction.

As illustrated in FIG. 5(C), the piercing tip 27 has a sharp front end part 27a for piercing the film which blocks the opening part of the well 22 of the test cartridge container 14, the opening part of a rear end part 27b is attachable to the nozzle 30 and, in the outer periphery of the rear end part 27b, a plurality of elongated protrusions 27c are provided in parallel to the axial direction. In addition, with these tips, the length of the small diameter tube or front end part is, for example, 1 cm to 10 cm, the length of the large diameter tube is, for example, 1 cm to 10 cm and the diameter of the particle is, for example, 0.1 mm to 3 mm. Hence, the inner diameter of the small diameter tube 26a has the size which can hold this particle in one row, and is, for example, about 0.2 mm to 6 mm.

Figure 6:
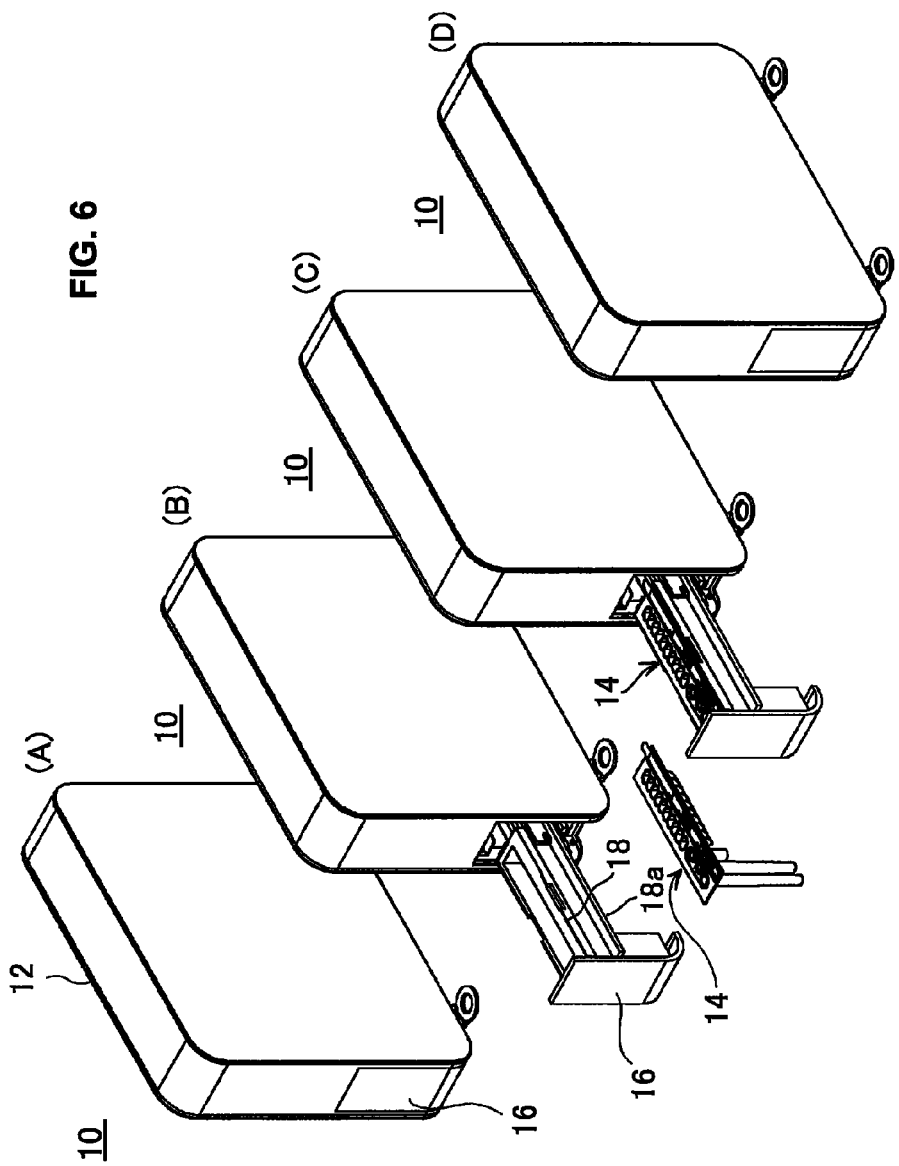
FIG. 6 is a processing flow view of the specimen testing device illustrated in FIGS. 1 and 2.

Then, the operation of the specimen testing device 10 according to the first embodiment will be described based on FIG. 6.

As illustrated in FIG. 6(A), in step S1, the fitting plate 16 of the housing 12 of the specimen testing device 10 is drawn forth by the hand. As illustrated in FIG. 6(B), in step S2, the loading box 18 is expanded to the outside of the housing 12. As illustrated in FIG. 6(C), in step S3, the test cartridge container 14 which accommodates a specimen of the test target, a test reagent and tips in advance is loaded in the loading box 18. In this case, in the seal 24 of the test cartridge container 14, the name of the patient belonging to the specimen information is hand-written, and test information showing test content is written in advance. As illustrated in FIG. 6(D), in step S4, the loading box 18 and loaded test cartridge container 14 are inserted and accommodated in the housing 12 by the hand.

In the state of FIG. 6(D), the following processing is performed.

In step S5, the nozzle head 15 is moved to the tip accommodation part 20 of the test cartridge container 14 to place the nozzle 30 above the piercing tip 27. The nozzle 30 is lowered along the Z axis direction to insert, push in and attach the front end of the nozzle 30 to the opening part of the piercing tip 27.

In step S6, the nozzle 30 to which the piercing tip 27 is attached is positioned sequentially above each well 22 of the test cartridge container 14, and then is lowered to pierce the film which covers the ten wells 22.

In step S7, when all wells 22 are pierced, the nozzle 30 moves to the position at which the piercing tip 27 of the tip accommodation part 20 is accommodated, a U-shaped groove of the tip detaching plate 48 is placed close to the nozzle 30 and the nozzle 30 is moved along an upper direction (Z axis direction) to attach and detach the piercing tip 27 to and from the inside of the cylindrical body 20c of the tip accommodation part 20.

In step S8, the nozzle 30 is moved above the position at which the dispenser tip 25 (or carrier sealing tip 26) of the tip accommodation part 20 is accommodated and is lowered along the Z axis direction, and the front end of the nozzle 30 is inserted, pushed in and attached to the opening part of the dispenser tip 25 (or the carrier sealing tip 26).

For example, processing of the specimen testing device 10 in case where an allergy test of a test subject is performed will be described.

Various allergen substances such as several types of allergen substances (antibodies) obtained from cedar pollen, ragweed, egg white, soy bean, house dust, ticks and fungus are fixed to the particles 26c of the carrier sealing tip 26. The particles 26c to which each allergic substance is fixed are sealed in advance at alignment positions matching the type of the fixed allergen substance. Further, the particles 26c to which no allergen substance of any type is fixed are also arranged between the particles 26c to which the allergen substances are fixed in the carrier sealing tip 26.

Further, a serum collected from the test subject as a specimen is accommodated in the well 22a of the test cartridge container 14, a peroxidase solution of a labeling enzyme is accommodated in the well 22b, and a luminol/hydrogen peroxide solution is accommodated in the well 22c as a substrate solution for chemiluminescence. Further, in the well 22d to well 22i, rinse solutions such as a phosphoric acid buffer solution or tris buffer solution are accommodated. The above arrangement of each particle 26c and the type of a reagent are displayed as test information, and information about the test subject is displayed as specimen information.

In step S9, the dispenser tip 25 is attached to the nozzle 30, the attached dispenser tip 25 is positioned at the well 22b to suck the peroxidase solution, and is moved to discharge the solution in the well 22a which accommodates the serum and maintain the solution for a certain period of time at a room temperature. By this means, a human IgE antibody in the serum is labeled by the peroxidase solution.

In step S10, the dispenser tip 25 is moved to the position at which the dispenser tip 25 of the tip accommodation part 20 of the test cartridge container 14 is accommodated, the U-shaped groove of the tip detaching plate 48 is placed close to the nozzle 30 and then the nozzle 30 is moved along the upper direction to attach and detach the dispenser tip 25 to and from the cylindrical body 20a of the tip accommodation part 20.

In step S11, the nozzle 30 is moved directly above the position at which the carrier sealing tip 26 of the tip accommodation part 20 is accommodated and is lowered along the Z axis direction, and the front end of the nozzle 30 is inserted, pushed in and attached to the opening part of the carrier sealing tip 26.

In step S12, the carrier sealing tip 26 is moved to the well 22d, and sucks and discharges, for example, 100 μliters of the rinse solution to perform rinsing.

In step S13, the carrier sealing tip 26 is moved to the well 22e, and sucks and discharges the rinse solution accommodated in the well 22e to perform rinsing.

In step S14, the carrier sealing tip 26 attached to the nozzle 30 is moved to the position of the well 22a, sucks the serum containing the human IgE antibody labeled by the peroxidase accommodated in the well 22a to the position of the large diameter tube 26b so as to fill the small diameter tube 26a of the carrier sealing tip 26 and make the serum contact the particles 26c, and causes a reaction between the human IgE antibody and allergen substance in the serum for about 30 minutes.

In step S15, the carrier sealing tip 26 is moved to the well 22f of the test cartridge container 14 and repeats suction and discharging, for example, about 100 μliters of the rinse solution accommodated in the well 22f ten times, is further moved to the well 22g of the test cartridge container 14 and is transported to the well 22g to repeat rinsing.

In step S16, the carrier sealing tip 26 is transported to the well 22c of the test cartridge container 14 to suck a luminol/hydrogen peroxide solution of a substrate solution to cause a reaction with a peroxidase solution of a labeling substance, and the carrier sealing tip 26 which produces luminescence is positioned directly above the semi-circular hole 36a of the optical measurement unit 17.

In step S17, the small diameter tube 26a of the carrier sealing tip 26 is inserted in the cavity portion formed with the semi-circular hole 36a and elongate hole 35a. In this case, the measurement plate 35 is moved in the backward direction to move the elongate hole 35a along the axial direction and place the elongate hole 35a closer, and the small diameter tube 26a of the carrier sealing tip 26 is lowered and is accommodated in the tip insertion part 34 to scan the particle 26c and measure a luminescent state per particle 26c.

In step S18, whether or not luminescence is produced is measured per particle 26c. Each particle 26c is associated with each allergic substance in advance in the alignment order, and the allergen substance bound with the labeled antibody is specified based on the luminescence. The measurement result is analyzed by a control unit of the board 52, is output to the thermal transfer printer mechanism 21, is printed as one item of the test information in the remarks space of the seal 24 by the printing head 21a and is displayed by numbers.

In step S19, the digital camera 28 captures an image of specimen information and test information on the seal 24 of the test cartridge container 14 as image data according to a command signal from the board 52. In this case, an analyzing unit of the control unit searches for data which can be analyzed, from the image data, when finding a two-dimensional barcode data showing the test content included in the test information, and analyzes the two-dimensional barcode data to obtain analyzed data, and the data synthesizing unit of the control unit synthesizes and stores the analyzed data and image data in a memory as data which can be output.

In step S20, the carrier sealing tip 26 attached to the nozzle 30 moves to the tip accommodation part 20, moves directly above the position at which the carrier sealing tip 26 is accommodated, and places the U-shaped groove of the tip detaching plate 48 close to the nozzle 30, and the nozzle 30 is moved in the upper direction to attach and detach the carrier sealing tip 26 to and from the inside of the cylindrical body 20b of the tip accommodation part 20.

In step S21, when testing of the specimen is finished, the loading box 18 in which the test cartridge container 14 is loaded is manually drawn forth from the housing 12, the seal 24 pasted on the test cartridge container 14 is peeled off and is stuck to a mat board for management which is additionally prepared and stored, and a new test cartridge container 14 is further loaded to the housing 12 while the test cartridge container 14 is discarded, so that it is possible to test a new specimen.

Subsequently, processing of the specimen testing device 10 in case where whether or not there is an allergen substance of food will be described.

For example, seven items of materials of mandatory labeling for Japanese food including egg, milk, wheat, buckwheat, peanut, shrimp and crab, and, for example, allergen substances selected from allergen substances (antibodies) obtained from eighteen items (peach, pork, chicken and beef) of recommended labeling for Japanese food are further fixed to the particles 26c in the carrier sealing tip 26. The particles 26c to which each allergen substance is fixed are sealed in advance after blocking is applied to an arrangement matching the type of the fixed allergen substance. Further, the particles 26c to which no allergen substance of any type is fixed are also arranged between the particles 26c to which the allergen substances are fixed in the carrier sealing tip 26.

Further, an extraction liquid (antigen) extracted from food is accommodated as a specimen in the well 22a of the test cartridge container 14, and various labeled antibodies labeled by a chemiluminescent substance HRP enzyme are accommodated in the well 22b. TMB which is a substrate solution for chemiluminescence is accommodated in the well 22c. A rinse solution or buffer solution is accommodated in the well 22d to well 22j. The arrangement of these particles 26c and the type of the reagent are displayed as test information, and information about the test subject is hand-written as specimen information.

In step S9', the nozzle 30 is moved directly above the position at which the carrier sealing tip 26 of the tip accommodation part 20 is accommodated and is lowered along the Z axis direction, and the front end of the nozzle 30 is inserted, pushed in and attached to the opening part of the carrier sealing tip 26.

In step S10', the carrier sealing tip 26 is moved to the well 22d, and sucks and discharges, for example, 100 μliters of the rinse solution to perform rinsing.

In step S11', the carrier sealing tip 26 is moved to the well 22a, sucks and discharges 20 μliters of the food extraction liquid of a specimen and contacts with the particles.

In step S12', the carrier sealing tip 26 is moved to the well 22e, and repeats suction and discharging 80 μliters of the buffer solution three hundred times to incubate at a room temperature for 30 minutes. When necessary, the buffer liquid of the temperature controlled by a temperature controller (described later) is preferably used.

In step S13', the carrier sealing tip 26 is moved to the well 22f and sucks and discharges 100 μliters of the rinse solution to perform rinsing, and, similarly, the carrier sealing tip 26 is moved to the wells 22g and 22h in which the rising solution is accommodated and sucks and discharges 100 μliters of the rinse solution to perform rinsing three times in total.

In step S14', the rinsed carrier sealing tip 26 is moved to the well 22b and repeats suction and discharging 100 μliters of the labeling antibody accommodated in the well 22b three hundred times to incubate for 30 minutes.

In step S15', the carrier sealing tip 26 is moved to the well 22*i* and sucks and discharges 100 µliters of the rinse solution to perform rinsing, and, similarly, the carrier sealing tip 26 is moved to the well 22*j* and sucks and discharges 100 µliters of the rinse solution to perform rinsing and the rinsed carrier sealing tip 26 is moved to the well 22*c* and sucks and discharges 60 µliters of the substrate solution to produce chemiluminescence.

The following processing is the same as in above step S17 to step S21, and therefore will not be described.

Figure 7:
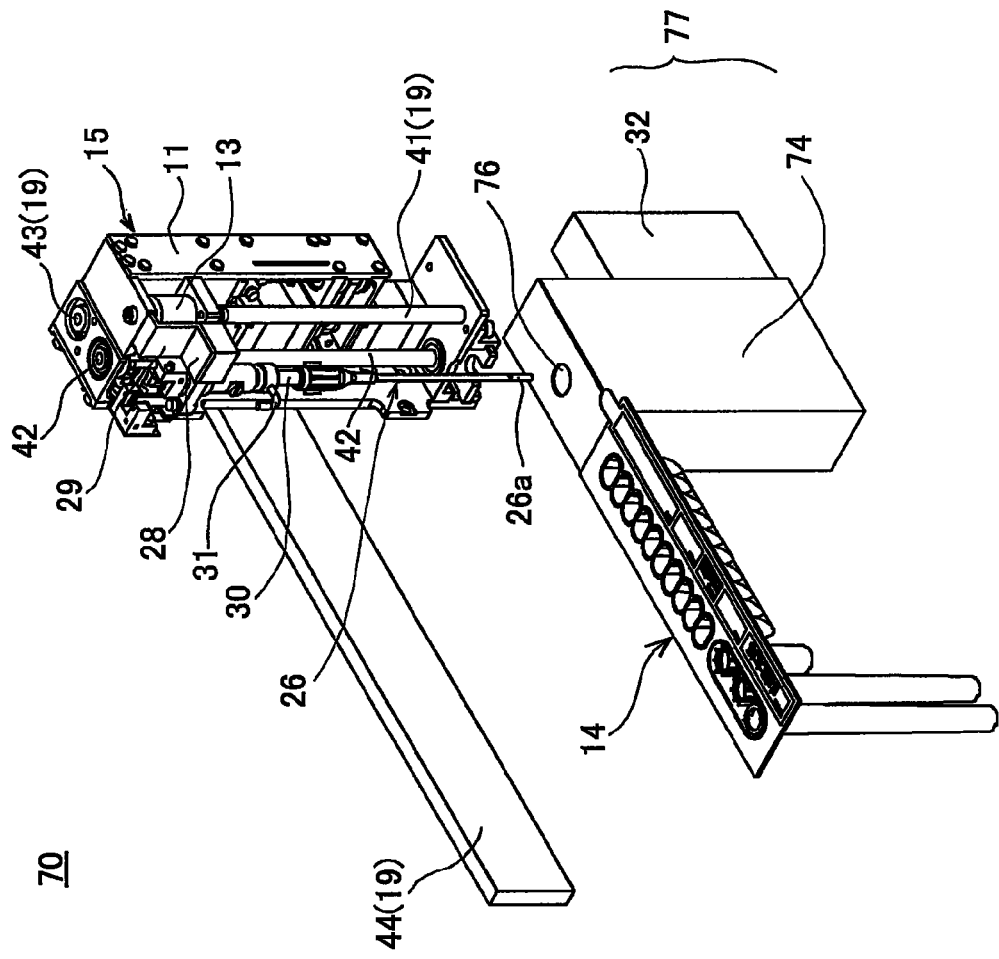
FIG. 7 is a perspective view illustrating that main components of a specimen testing device according to a second embodiment of the present invention are taken out of a housing.

Next, FIG. 7 illustrates a specimen testing device 70 according to a second embodiment.

The specimen testing device 70 differs in using an optical measurement unit 77 instead of the optical measurement unit 17 used in the specimen testing device 10 according to the first embodiment.

The optical measurement unit 77 has: the photoelectric unit 32 which has at least one photoelectric element; and a scanning/measuring unit 74 which has a hole 76 in which the small diameter tube 26*a* of the carrier sealing tip 26 can be inserted, and in which each of the light receiving ends 33*a*, 33*b* and 33*c* of the optical fibers 37*a*, 37*b* and 37*c* provided to surround the small diameter tube 26*a* of the carrier sealing tip 26 inserted through the hole 76 and connected with the photoelectric unit 32 is provided to move along the axial direction of the small diameter tube 26*a* inserted through the hole 76. That is, the optical measurement unit 77 differs from the optical measurement unit 17 according to the first embodiment in that each of the light receiving ends 33*a*, 33*b* and 33*c* is not fixed to the housing 12 upon measurement, and is relatively movable.

Figure 8:
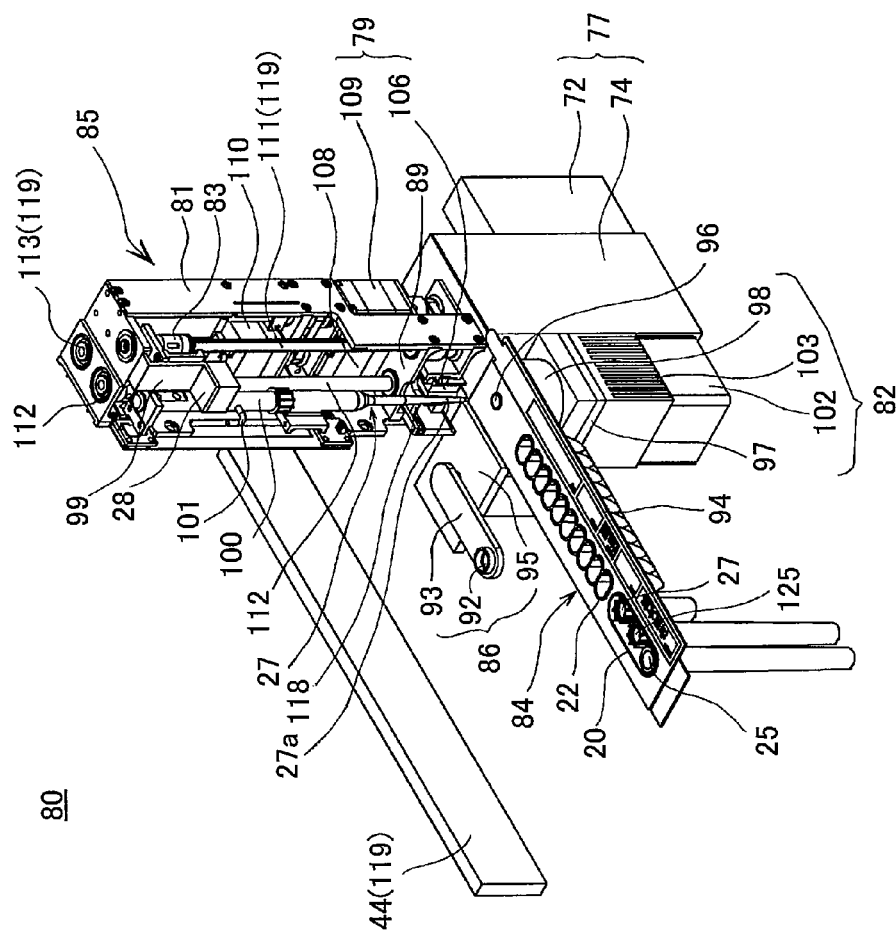
FIG. 8 is a perspective view illustrating that main components of a specimen testing device according to a third embodiment of the present invention are taken out of a housing.

FIG. 8 illustrates a specimen testing device 80 according to a third embodiment.

The specimen testing device 80 differs from the specimen testing devices 10 and 70 according to the first and second embodiments in mainly having: a magnetic member 79 which has a magnet 106 provided to contact and separate from the small diameter tube 25 to apply and remove the magnetic force to and from the small diameter tube 25*a* of the dispenser tip 25; a temperature controller 82 which controls the temperature of a well 96 provided in a test cartridge container 84; and a cap moving mechanism 86 which blocks the well 96 by means of a cap 92.

The specimen testing device 80 is mounted in the housing 12 similar to the specimen testing devices 10 and 70 according to the first and second embodiments. The housing 12 has: a test cartridge container 84 in which a tip accommodation part 20 which accommodates a plurality of types (three types including two types of dispenser tips 25 and 125 having different volumes and piercing tip 27 with this example) of tips, a plurality of (ten with this example) wells 22 which accommodate or can accommodate a specimen and one, two or more reagent solutions, and the well 96 which is provided spaced apart from the well 22 and of which temperature is controlled are aligned in one row and provided, which displays specimen information for identifying or managing the specimen and test information showing test content on a seal 94 of a visible recording medium, and which is formed with a translucent member; an automatic testing unit (85 and 19) which causes a reaction of the specimen and the reagents accommodated in the test cartridge container 84 to obtain predetermined luminescence; an optical measurement unit 177 which measures the luminescence produced as a result of the test in the automatic testing unit; a digital camera 28 which captures an image of content displayed on the test cartridge container 84 including the specimen information and test information to obtain image data; a thermal transfer printer mechanism 21 (see FIG. 1) which can print a test result on blank spaces of the seal 94 of the test cartridge container 84 as a writing mechanism; and the magnetic member 79; the temperature controller 82; the cap moving mechanism 86; and a board 52 which has an integrated circuit such as a CPU for controlling the automatic testing unit (85 and 19), optical measurement unit 177, digital camera 28, thermal transfer printer mechanism 21, magnetic member 79, temperature controller 82 and cap moving mechanism 86.

The test cartridge container 84 is provided to be manually drawn forth from the housing 12 to the outside of the housing 12 as illustrated in FIGS. 1 and 2. In addition, the volume of the well 96 which controls the temperature of the test cartridge container 84 is, for example, 0.2 cc.

The automatic testing unit (85 and 19) has: a nozzle head 85 of a dispenser; and a moving mechanism 119 which can move the nozzle head 85 with respect to the test cartridge container 84 accommodated in the housing 12.

The nozzle head 85 of the dispenser has: a X axis moving body 81 which can move in the X axis direction corresponding to a longitudinal direction with respect to the test cartridge container 84 accommodated in the housing 12 by means of the moving mechanism 119; and a Z axis moving body 83 which is provided to be guided by a guide column 111 in up and down directions with respect to the X axis moving body 81 and moved. To the X axis moving body 81, a nut part jointed to the Z axis moving body 83 is screwed and a Z axis moving ball screw 113 described later which moves the Z axis moving body 83 in the up and down directions is rotatably attached, and the guide column 111 and a support plate 89 which is attached through the guide column 111 are attached.

The nozzle head 85 has: the nozzle 100 which is attached to the Z axis moving body 83, and in communication with a cylinder which sucks and discharges gas through an air rubber tube 101 which is provided to project from a lateral face; a motor 110 which drives a piston in the cylinder; and a ball screw 112 which is rotatably attached.

Further, the support plate 89 which is attached to the X axis moving body 81 rotatably supports the ball screw 113 and, beneath the support plate 89, supports movably in front and back directions a tip detaching plate 118 in which a U-shaped hole greater than the diameter of the nozzle 100 and smaller than the outer diameter of the thickest portion of the tip is formed to attach and detach a tip such as the dispenser tip 25 to and from the nozzle 100 and the magnet 106 which is provided to contact and separate from the small diameter tube 25*a* of the dispenser tip 25 attached to the nozzle 100 and which can apply and remove the magnetic force to and from the interior of the small diameter tube 25*a* from an outside, and, on the upper side of the support plate 89, a motor 108 which drives the tip detaching plate 118 and a motor 109 which drives the magnet 106 are attached to the X axis moving body 81. The magnet 106 and motor 109 correspond to the magnetic member 79.

The digital camera 28 is attached to the X axis moving body 81 through a camera support plate 99, and captures an image by moving the nozzle head 85 to a position at which the digital camera 28 can capture the entire specimen information and test information on the seal 94 of the test cartridge container 84 accommodated in the housing 12.

The moving mechanism 119 which moves the nozzle head 85 of the dispenser with respect to the test cartridge container 84 accommodated in the housing 12 has: a rail 44 which engages with and guides the X axis moving body 81 of the nozzle head 85 in the longitudinal direction, that is, the X axis direction of the cartridge container 84; a X axis moving motor 58 (see FIG. 1) which moves the nozzle head 85 along the X axis direction; the guide column 111 which guides the X axis moving body 83 in the up and down directions, that is, the Z axis direction; the Z axis moving ball screw 113; and a Z axis moving motor. In addition, the ball screw 112 and motor 110 correspond to an suction/discharging mechanism. Further, the guide column 111, the Z axis moving ball screw 113 and the Z axis moving motor correspond to the Z axis moving mechanism in the moving mechanism.

In addition, the specimen testing device 80 according to the present embodiment also has the thermal transfer printer mechanism 21 which is a writing mechanism. The thermal transfer printer mechanism 21 is as described above.

The cap moving mechanism 86 has: a cap 92 which covers the opening part of the well 96; an arm 93 in which the cap 92 is provided at one end and the other end is axially supported by a rotary shaft to rotate 90 degrees by a rotary shaft; and a rotation driving unit 95 which has a motor driving the rotary shaft.

Further, the specimen testing device 80 can further press, shake or move the cap 92 which blocks the opening part of the well 96 of the test cartridge container 84, using the nozzle 100 which can be pressed, shaken or moved by the moving mechanism 119 including the Z axis moving mechanism along the Z axis direction, X axis direction and Y axis direction. That is, the nozzle 100 which is driven by the moving mechanism 119 including the Z axis moving mechanism corresponds to a cap-blocked-duration functioning mechanism. In this case, the cap 92 is preferably biased and supported by the elastic force with respect to the rotary shaft in the Z axis direction.

Figure 9:
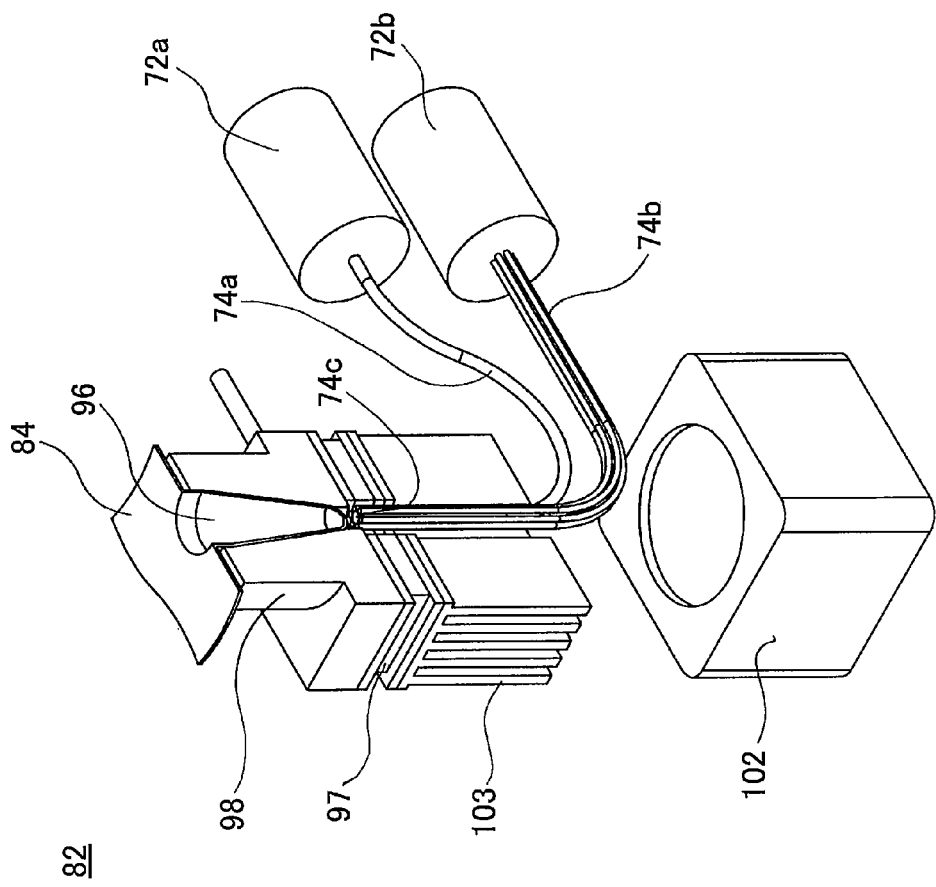
FIG. 9 is an enlarged perspective view illustrating an optical measurement unit and a temperature controller illustrated in FIG. 8 partially cut out.

As illustrated in FIG. 9, the temperature controller 82 has: a temperature control block 98 in which a tapered fitting hole having the shape and size fitting with the well 96 of the test cartridge container 84 which is the well accommodation hole is bored and provided in the center; a peltier element unit 97 which has a peltier element which is provided in contact with the temperature control block 98 and which is a heating/cooling unit; a fin 103 which is provided below the peltier element unit 97; and a fin accommodation frame body 102 which is provided below the fin 103, and a radiation optical fiber 74a and six light receiving optical fibers 74b extending from the bottom of the fitting hole, passing the fin 103 through the peltier element part 97 and one end of the radiation optical fiber 74a are connected with an excitation light source 75b, one end of the light receiving optical fiber 74b is connected with the photoelectron multiplying tube 72b, and the other ends 74c of these optical fibers 74a and 74b are bundled around the radiation optical fiber and provided such that the front ends are positioned in the bottom of the fitting hole which is the well accommodation hole.

Meanwhile, the optical fibers 74a and 74b pass a fiber accommodation part 174 of the optical measurement unit 177, and are connected with the excitation light source 72a and photoelectron multiplier tube 72b built in the photoelectric/light source unit 72.

Next, the operation of the specimen testing device 80 according to the third embodiment will be described.

Step S31 to step S38 are the same as step S1 to step S8 except that the nozzle head 85 is used instead of the nozzle head 15, the nozzle 100 is used instead of the nozzle 30 and the test cartridge container 84 is used instead of the test cartridge container 14.

In the state of FIG. 6(D), the following processing is performed.

Hereinafter, an operation of controlling the temperature of DNA or genome and performing PCR processing instead of conducting an allergy test described in the first embodiment will be described.

In the well 22a of the test cartridge container 84, for example, a specimen such as a mucous membrane of the mouth collected from the test subject is accommodated. In the well 22b, a genome extraction reagent is accommodated.

In the well 22c, a magnetic particle suspension is accommodated. In the well 22d, a separate solution is accommodated. The well 22e is empty. In the well 22f to well 22i a primer containing solution which is a PCR reagent and rinse liquid are accommodated. In the well 22j, mineral oil is accommodated. Further, the tip accommodation part 20 accommodates the two types of dispenser tips 25 and 125 and piercing tip 27.

In step S39, the nozzle 100 is moved to the position of the dispenser tip 25 accommodated at the end of the tip accommodation part 20, and is lowered to be attached to the nozzle 100 to extract the genome, and the dispenser tip 25 is moved to the well 22b by the moving mechanism 119 to suck a corresponding extraction reagent using the suction/discharging mechanism. The dispenser tip 25 is moved to the well 22a which accommodates the specimen, and discharges in the well 22a the liquid sucked in the dispenser tip 25. Further, the dispenser tip 25 is moved to the well 22c to suck the magnetic particle suspension, and is moved to the well 22a to discharge the magnetic particle suspension, and, if there are reagents which are necessary to perform extraction, the reagents are transported to the well 22a using the dispenser tip 25 and discharged. These mixed liquids accommodated in the well 22a are repeatedly sucked and discharged to be reacted while being stirred and incubated, and the extracted DNA is bound to the surfaces of the magnetic particles and is caught.

In step S40, the magnet 106 is placed close to the small diameter tube 25a of the dispenser tip 25 using the magnetic member 79 to produce the magnetic field therein, and the magnetic particles are attracted to the inner wall of the small diameter tube 25a to separate DNA.

In step S41, the dispenser tip 25 for genome extraction is moved by the moving mechanism 119 while the magnetic particles catching the DNA are attracted to the inner wall, and is positioned over the well 22d which accommodates the separate solution, and the front end outlet part of the dispenser tip 25 is inserted in the well 22d and repeats sucking and discharging the separate solution with the magnetic particles attracted to the inner wall to separate the DNA from the magnetic particles. The DNA solution containing the DNA separated from the magnetic particles is discharged into and accommodated in the empty well 22e, and the dispenser tip 25 for genome extraction is transported to the original accommodation position in the tip accommodation part 20 while the magnetic particles are attracted to the inner wall to attach and detach using the tip detaching plate 118.

In step S42, the nozzle head 85 is moved, the nozzle 100 of the nozzle head 85 is moved to a new dispenser tip 125 for PCR accommodated at the middle position in the tip accommodation part 20, and the nozzle 100 is lowered by the Z axis moving mechanism to insert and attach the nozzle 100 in and to the attachment opening part of the accommodated dispense tip 125 for PCR.

In step S43, the nozzle head 85 is moved, and the arm 93 is rotated 90 degrees as illustrated in FIG. 9 to open the cap 92 and expose the opening part of the well 96 to the outside. Next, using the dispenser tip 125 for PCR, reagents for PCR accommodated in the well 22f to well 22i such as a primer containing solution labeled by a fluorescent material is sucked, dispensed and accommodated in the well 96. The above process is repeated until dispensing of the required reagents is finished.

In step S44, the dispenser tip 125 is rinsed, and then the nozzle head 85 is moved to suck the extracted DNA liquid accommodated in the well 22e to dispense in the well 96. Then, the dispenser tip 125 is used and moved to the well 22j, and sucks the mineral oil and discharges the mineral oil in the well 96 to introduce.

In step S45, the cap 92 is rotated 90 degrees to cover the opening part of the well 96.

In step S46, the nozzle 100 is lowered to press the cap 92 using the Z axis moving mechanism.

In step S47, the temperature controller 82 controls the temperature of the well 96 according to a PCR method. The temperature control according to the PCR method is directed to setting the temperature of the well 96 to 94° C. to denature two strands of DNA of the administered specimen to a single strand, and set the temperature of the well 96 to 50° C. to 60° C. to anneal and hybridize the single strand of DNA and primer. Next, a cycle of an operation of performing incubation by synthesizing complementary DNA strands to a single strand and setting the temperature to 74° C. is repeated a predetermined number of times, and temperature control is performed for about several minutes.

In this case, excitation light is radiated using the optical fibers 74a and 74b provided in the fitting hole which is the well accommodation hole of the temperature control block 98, and the fluorescence intensity to be produced is received by the optical fiber 74b and is converted into an electric signal by the photoelectron multiplier tube 72b to measure the fluorescence intensity.

In step S48, the measurement result is analyzed by the control unit of the board 52, is output to the thermal transfer printer mechanism 21, is printed as one item of the test information in the remarks space of the seal 24 by the printing head 21a and is displayed by numbers.

In step S49, the digital camera 28 captures an image of specimen information and test information on the seal 94 of the test cartridge container 84 as image data according to a command signal from the board 52. In this case, an analyzing unit of the control unit searches for data which can be analyzed, from the image data, when finding a two-dimensional barcode data showing the test content included in the test information, and analyzes the two-dimensional barcode data to obtain analyzed data, and the data synthesizing unit of the control unit synthesizes and stores the analyzed data and image data in a memory as data which can be output.

In step S50, the dispenser tip 125 attached to the nozzle 100 moves to the tip accommodation part 20, is moved directly above the position at which the dispenser tip 125 is accommodated, and places the U-shaped groove of the tip detaching plate 118 close to the nozzle 100, and the nozzle 100 is moved in the upper direction to attach and detach the dispenser tip 125 to and from the inside of the cylindrical body 20b of the tip accommodation part 20.

In step S51, when testing of the specimen is finished, the loading box 18 in which the test cartridge container 84 is loaded is manually drawn forth from the housing 12, the seal 94 pasted on the test cartridge container 84 is peeled off and is stuck to a mat board for management which is additionally prepared and stored, and a new test cartridge container 84 is further loaded to the housing 12 while the test cartridge container 84 is discarded, so that it is possible to test a new specimen. According to the present embodiment, the cap 92 can be pushed using the moving mechanism, so that it is possible to reliably block the opening part of the well 96 and easily prevent dew condensation and release the cap 92.

Figure 10:
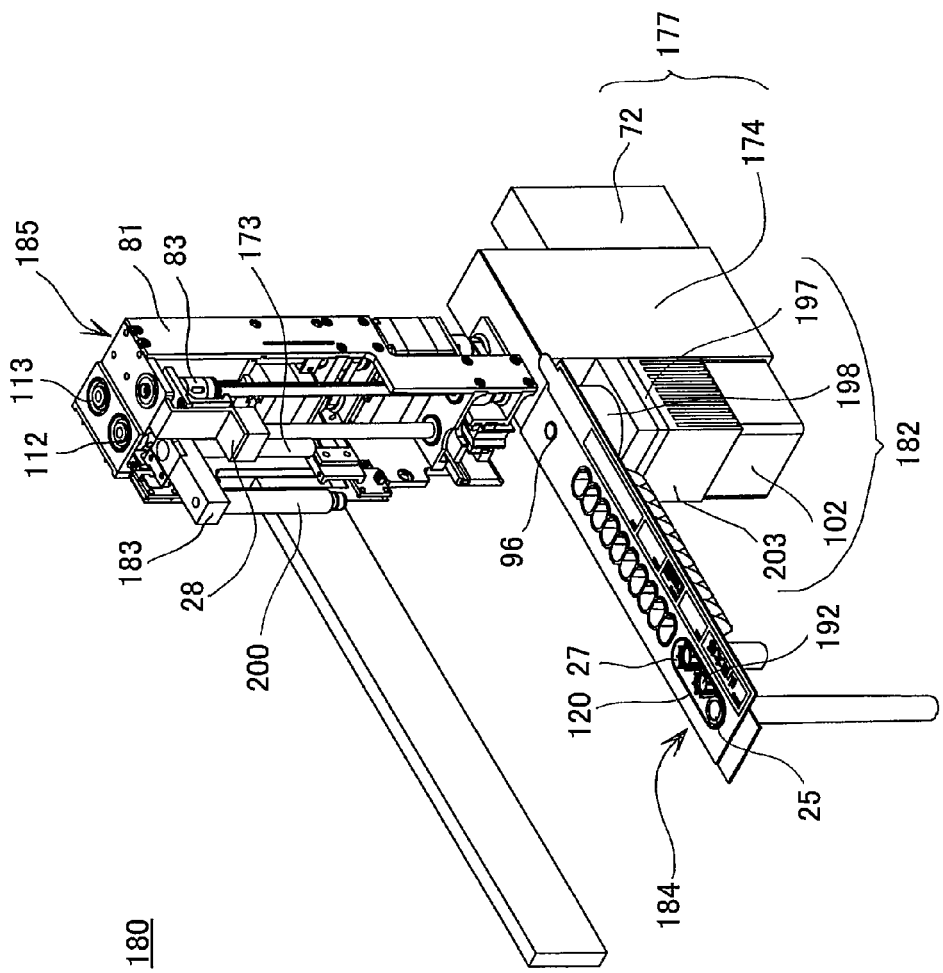
FIG. 10 is a perspective view illustrating that main components of a specimen testing device according to a fourth embodiment of the present invention are taken out of a housing.
Figure 11:
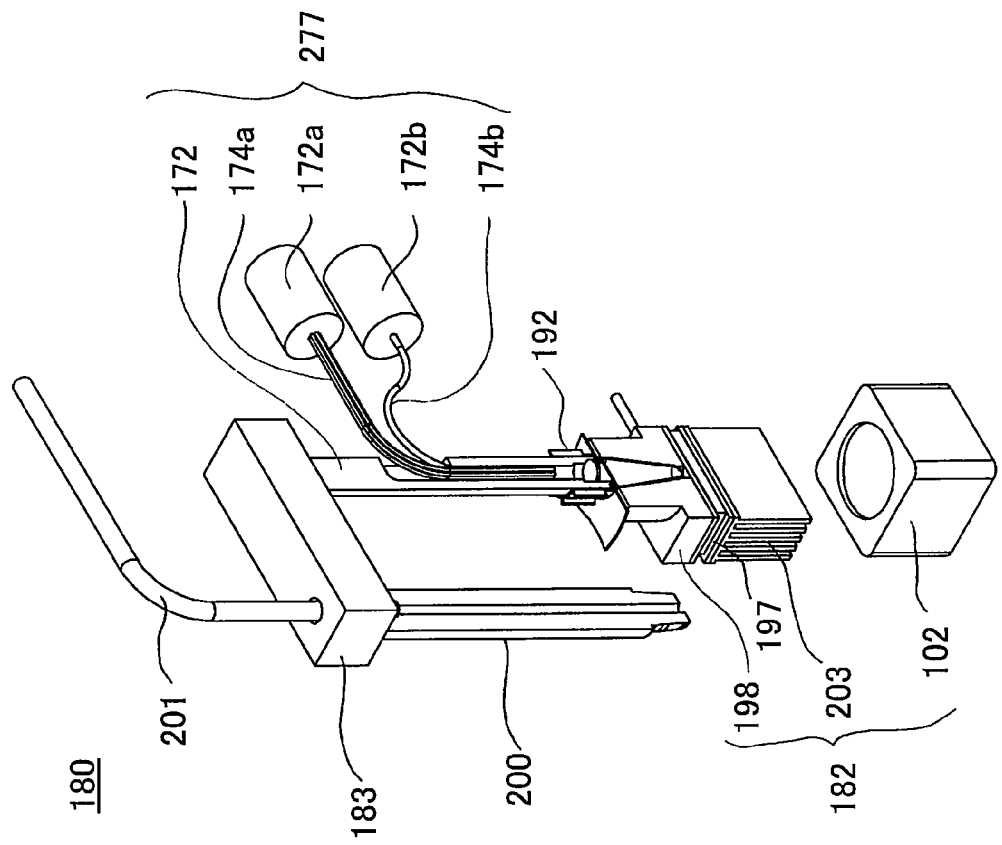
FIG. 11 is an enlarged perspective view illustrating an optical measurement unit and a temperature controller illustrated in FIG. 10 partially cut out.

FIGS. 10 and 11 illustrate a specimen testing device 180 according to a fourth embodiment.

In addition, the same components as in the specimen testing device 80 illustrated in FIG. 8 will be assigned the same reference numerals or will not be described without assigning the reference numerals.

The specimen testing device 180 differs from the specimen testing device 80 according to the third embodiment illustrated in FIG. 8 in that the nozzle head 185 has: a nozzle 200 to which the dispenser tip 25 in communication with the cylinder which sucks and discharges gas through an air rubber tube 201 are attachable; a nozzle support body 183 which interlocks with the Z axis moving body 83 which can move in the Z axis direction, and to which the nozzle 200 is attached; and a measurement rod 172 (see FIG. 11) in which the end of the light receiving optical fiber 174a and the end of the radiation optical fiber 174b are provided to measure luminescence from above a translucent cap 192 which covers the opening part of the well 96 of the test cartridge container 184 attached to the nozzle support body 183.

Additionally, the specimen testing device 180 differs from the specimen testing device 80 according to the third embodiment in that the cap moving mechanism 86 is not provided, and the cap 192 is accommodated in advance in the tip accommodation part 120 of the test cartridge container 184 in place of the carrier sealing tip 26, and is attached to the front end of the nozzle 200 or front end of the measurement rod 172 by lowering the nozzle 200 and the measurement rod 172 by the Z axis moving mechanism and is used upon pressing or upon measurement. Thus, the test cartridge container 184 also differs in that the cap 192 can be accommodated in the tip accommodation part 120.

Further, as illustrated in FIG. 11, an optical measurement unit 277 and the temperature controller 182 differ from the optical measurement unit 177 and temperature controller 82 according to the third embodiment.

With the optical measurement unit 277, the end of the light receiving optical fiber 174a and the end of the radiation optical fiber 174b are provided in the measurement rod 172, the other end of the light receiving optical fiber 174a is connected with the photoelectric element 172a and the other end of the radiation optical fiber 174b is connected with the light source unit 172b.

Further, the temperature controller 182 only has: a temperature control block 198 in which a tapered fitting hole having the shape and size fitting with the well 96 of the test cartridge container 184 is bored and provided in the center as the well accommodation hole; a peltier element unit 197 which has a peltier element which is provided in contact with the temperature control block 198 and which is a heating/cooling unit; and a fin 203 which is provided below the peltier element unit 197, and a fin accommodation frame body 102 which is provided below the fin 203 and the ends of optical fibers are not provided in the bottom of the fitting hole and the optical fibers do not pass the fin 203.

Figure 12:
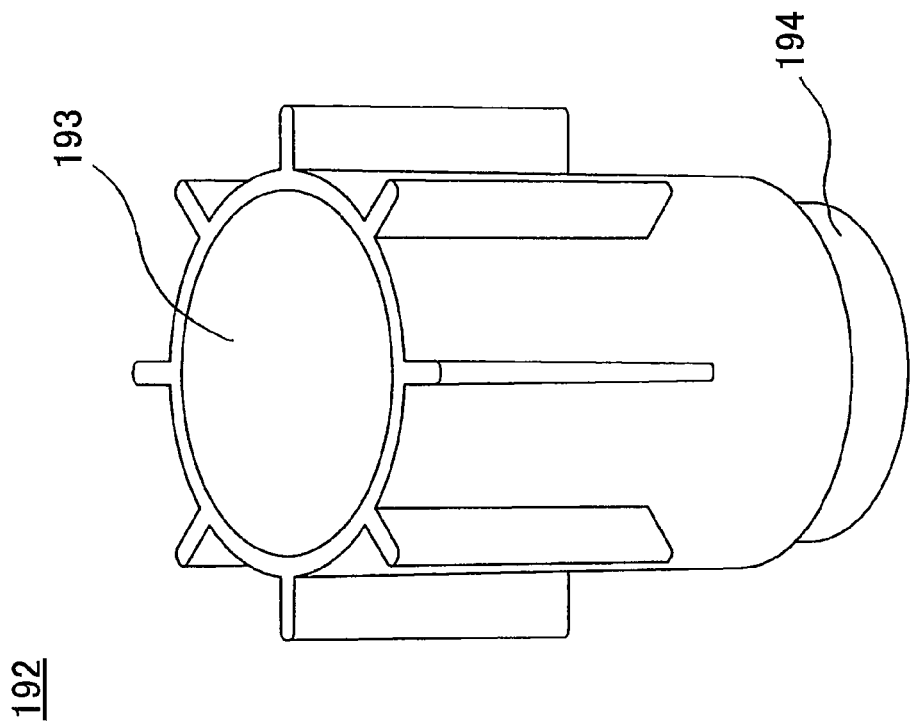
FIG. 12 is an enlarged perspective view illustrating a cap illustrated in FIG. 11.
Figure 13:
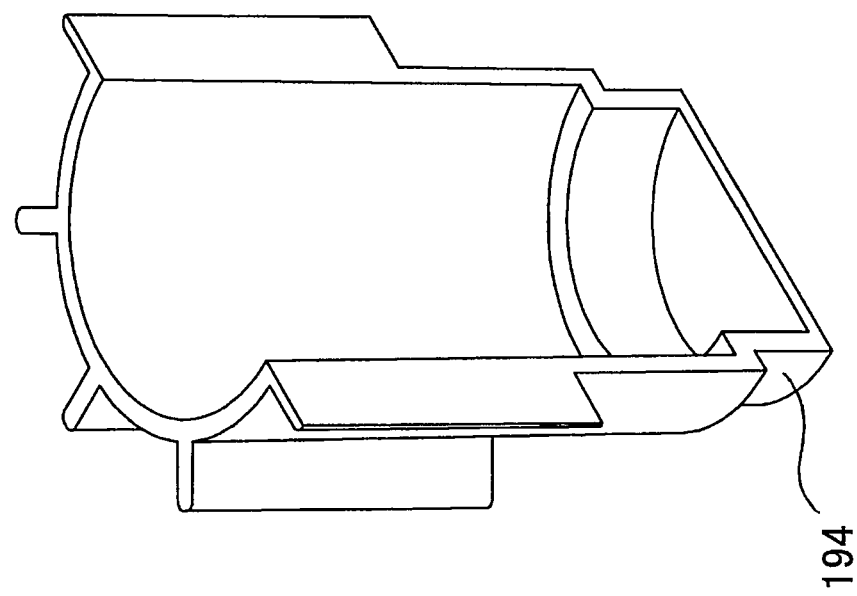
FIG. 13 is a perspective view of a cap illustrated in FIG. 12 partially cut out.

FIGS. 12 and 13 illustrate the cap 192. The cap 192 has: an attachment opening part 193 to which the measurement rod 172 and nozzle 200 can be attached; and the fitting part 194 which fits to the opening part of the well 96. With the device according to the present embodiment, the cap can block the opening part of the well 96 without providing the cap moving mechanism, so that it is possible to simplify the structure of the device. Further, if there is a concern that the cap contaminates a specimen, the cap can be accommodated in the test cartridge container and discarded together with a test cartridge container after the test is finished like a tip, so that it is possible to provide safe management.

Figure 14:
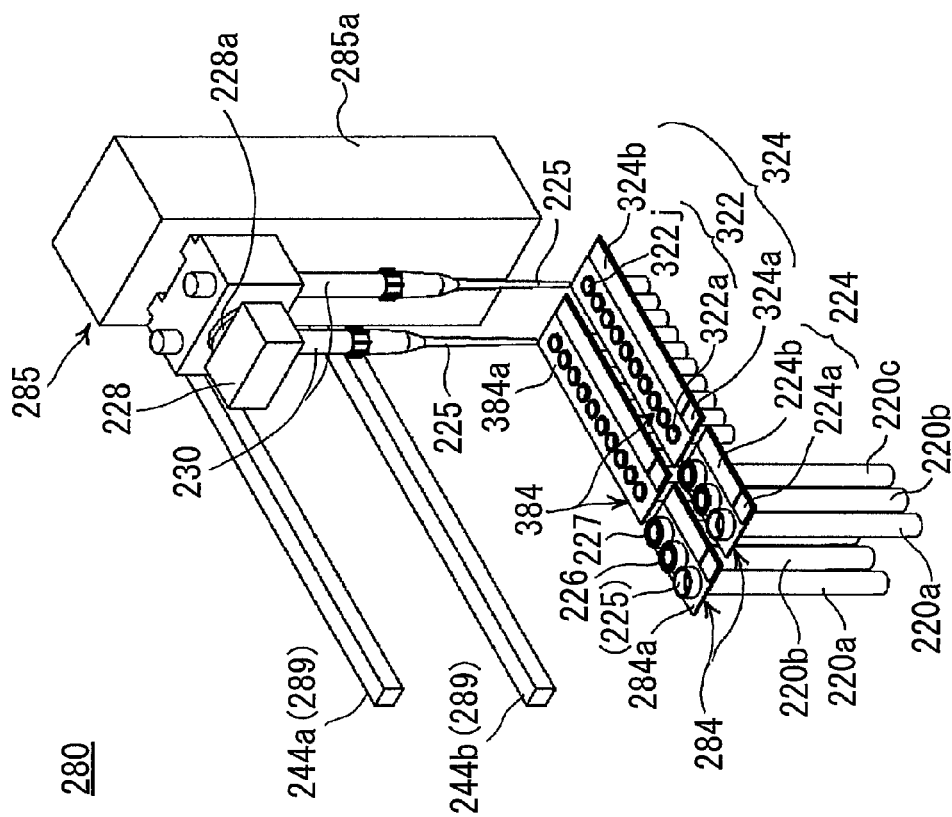
FIG. 14 is a pattern diagram illustrating that main components including four test cartridge containers of a specimen testing device according to a fifth embodiment of the present invention are taken out of a housing.

Next, a specimen testing device according to a fifth embodiment will be described based on FIG. 14.

A specimen testing device 280 according to the present embodiment has: two test cartridges 284 which are provided in housings of, for example, about 250 to 400 mm long (X axis direction), 140 to 200 mm wide (Y axis direction) and 300 to 500 mm high (Z axis direction), in which tip accommodation parts 220a, 220b and 220c which accommodate a specimen and a plurality of types (three types with this example) of tips which are one, two or more testing tools used to test the specimen are aligned in a row, which displays specimen information for identifying or managing the specimen and test information showing test content on a seal 224 which is a visible recording medium, and which are aligned in parallel; two test cartridge containers 384 in which a well 322 which accommodates and can accommodate a specimen and one, two or more reagent solutions used to test the specimen and which is a plurality of (ten with this example) accommodation parts is provided in one row, which displays specimen information for identifying or managing the specimen and test information showing test content on a seal 324 which is a visible recording medium, and which are formed with translucent members and aligned in parallel; an automatic testing unit (285 and 289) which causes a reaction of the specimen and the reagents accommodated in the two test cartridge containers 384 to obtain a predetermined optical state (for example, luminescence); an optical measurement unit which measures the optical state produced as a result of the test in the automatic testing unit; a digital camera 228; a thermal transfer printer mechanism which can print a test result on blank spaces of the seals 224 and 324 of the test cartridge containers 284 and 384; and a board which has an integrated circuit such as a CPU for controlling the automatic testing unit (285 and 289), the optical measurement unit, the digital camera 228 and the thermal transfer printer mechanism. 285a individually denotes a unit which mainly has a Z axis moving mechanism which moves the nozzle 230 in the Z axis direction.

Meanwhile, with the two cartridge containers 284, dispenser tip 225, carrier sealing tip 226 and piercing tip 227 which are a plurality of types (three types with this example) of tips of the testing tools are accommodated or can be accommodated in each of the tip accommodation parts 220a, 220b and 220c. The dispenser tips 225 are already attached to the nozzle 230 of the nozzle head 285, and therefore the accommodation parts 220a are empty.

With the two cartridge containers 284, the opening parts of the tip accommodation parts 220a, 220b and 220c are provided in a base plates 284a. In the seal pasting area which is a medium attaching part of the base plate 284a, the seal 224 is detachably pasted which has a specimen information space 224a and a test information space 224b showing test content. Meanwhile, in the specimen information space 224a, a QR code is printed in advance and a space to be filled by hand writing is provided and, in the test information space 224b, test information is printed in advance and a space to be filled by hand writing or a blank space for printing is provided. Similarly, with the two cartridge containers 384, the base plates 384a have wells 322a to 322j which accommodate ten reagent solutions and specimen solutions. In the seal pasting area which is a medium attaching part of the base plate 384a, the seal 324 is detachably pasted which has a specimen information space 324a and a test information space 324b showing test content. Meanwhile, in the specimen information space 324a, a QR code is printed in advance and a space to be filled by hand writing is provided and, in the test information space 324b, test information is printed in advance and a space to be filled by hand writing or a blank space for printing is provided.

In addition, all cartridge containers 284 and 384 aligned in the specimen testing device have common content of test information when the cartridge containers 284 and 384 are used for the same test. Further, although the test cartridge containers 284 and 384 aligned in a row (along the X axis direction) have common specimen information, the test cartridge containers 284 and 384 in the other row support a different specimen, these have specimen information different from the above specimen information.

For the automatic testing unit (285 and 289), the two nozzles 230 and 230 are provided, and each nozzle 230 is detachably attached with the dispenser tip 225 and each dispenser tip 225 is provided to move along the cartridge containers 284 and 384 in two rows. In addition, 244a and 244b denote rails which move the nozzle head 285 in the X axis direction and belongs to the moving mechanism 289.

In addition, the digital camera 228 is provided to be rotated a certain angle by a rotating mechanism 228a having the rotary shaft along the X axis direction, so that one digital camera 228 alone can cover the test cartridge containers 284 and 384 in the two rows. Further, the optical measurement unit, thermal transfer printer mechanism and optical measurement unit are also provided to move in the Y axis direction, so that one of the optical measurement unit, thermal transfer printer mechanism or optical measurement unit alone can support the test cartridge containers in the two rows, thereby making the device scale compact. According to the present embodiment, a plurality of tests can be processed in parallel, so that it is possible to perform efficient and quick processing.

The above-described embodiments are specifically described for better understanding of the present invention, and by no means limit other embodiments. Consequently, the present invention can be changed within a range without changing the spirit of the invention. Although, for example, cases of allergen substances, food and DNA have been described with the above embodiments, the present invention is naturally applicable to other tests of protein, sugar chains, DNA substances and RNA. Further, the numerical values, the number of times, shape the number of items and amount used in the above description are by no means limited to the above cases.

Further, types of tips, a cap and rod which need to be accommodated as a configuration of the test cartridge container, the structure and the number of tips, cap and rod, the number of or volume of wells, and content of specimen information and test information are only examples, and these can be adequately changed according to a specimen and test content.

Further, the above components such as each nozzle head, each type of tips, each cap, each nozzle, each temperature controller, each optical measurement unit, each test cartridge container and magnetic members are appropriately deformed and can be combined at random.

For example, it is possible to use the carrier sealing tip and use the test cartridge container which has wells of which temperature are controlled, and the temperature controller. Further, the above reagent, specimen and processing process are only examples, and other reagents, specimens and processing processes can be naturally used.

Although only cases have been described where one row or two rows of test cartridge containers are loaded in the specimen testing device and used, the present invention is by no means limited to this case and the present invention is naturally applicable to three or more rows of test cartridge containers. Further, when two rows of test cartridge containers are loaded and used, the present invention is by no means limited to this case, the test cartridge containers used in the first embodiment may be naturally aligned, loaded and used.

INDUSTRIAL APPLICABILITY

The present invention relates to a specimen testing device and method, is directed to testing specimens collected from patients and optically measuring and recording test results, and is applicable in various fields such as the fields in which handling of biomacromolecules and low molecules of gene, immune system, amino acid, protein and sugar, such as biochemistry, an industrial field, an agricultural field such as food, agrotechnology and seafood processing, a pharmaceutical field, and a medical field such as hygiene, health, immunity, disease and heredity.

DESCRIPTION OF REFERENCE NUMERALS 10, 70, 80, 180, 280 Specimen testing device
14, 84, 184, 284, 384 Test cartridge container
15, 85, 185, 285 Nozzle head
17, 77, 177, 277 Optical measurement unit
24, 94, 224 Seal
25, 125, 225 Dispenser tip
26, 226 Carrier sealing tip (solid-phase built-in tip)
28, 228 Digital camera
30, 100, 200, 230 Nozzle
92, 192 Cap

The invention claimed is:

1. A specimen testing device comprising:
one, two or more test cartridge containers which comprise a plurality of accommodation parts which accommodate or can accommodate a specimen and one, two or more reagent solutions and testing tools used for testing the specimen, and which visibly display specimen information for identifying or managing the specimen and test information showing test content;
an automatic testing unit which is attached with or supports the testing tools and which causes a reaction of the specimen and the reagent solution accommodated in the test cartridge containers to obtain a predetermined optical state;
an optical measurement unit which measures the optical state obtained by the automatic testing unit; and
a digital camera which captures an image of content as one image at one image capturing position, including the specimen and test information displayed on the one, two or more test cartridge containers, to obtain image data;
wherein a part of pieces of the specimen and test information are visibly displayed as a code data corresponding to the part of pieces of the specimen and test information on the cartridge containers;
wherein the digital camera includes: an analyzing unit which analyzes whether or not there is code data in the obtained image data, and when the code data is specified, converting the code data into analyzed data matching the code data, to obtain analyzed data; and a data synthesizing unit which synthesizes the image data and the analyzed data to output;
wherein the analyzed data matches the part of pieces of the specimen and test information;
wherein the automatic testing unit has a dispenser, the dispenser including: a suction/discharging mechanism which can suck and discharge gas; a nozzle which communicates with the suction/discharging mechanism and is detachably attachable to each of the testing tools; and a moving mechanism which is provided with the nozzle relatively movably with respect to the test cartridge containers;
wherein the testing tools comprise a dispenser tip and a solid-phase built-in tip which is built in a state where an interior of the solid-phase built-in tip can be measured from outside of the solid-phase built-in tip, the test cartridge containers accommodate or can accommodate the dispenser tip and the solid-phase built-in tip so that the nozzle can be attached to each of the testing tools, and the optical measurement unit can optically measure the interior of the solid-phase built-in tip from outside of the solid-phase built-in tip;
wherein the test information comprises information associated with the solid-phase built-in tip;
wherein the solid-phase built-in tip is a carrier sealing tip having a large diameter tube attachable to the nozzle and a small diameter tube in which carriers of specified fixed positions are sealed in one row, the small diameter tube communicating with the large diameter tube and having a size that allows insertion in one or more of the plurality of accommodation parts;
wherein, with the carriers sealed in the small diameter tube of the carrier sealing tip, chemical substances and the specified fixed positions of the carriers are associated to be measured from outside the carrier sealing tip; and
wherein the optical measurement unit optically measures the interior of the carrier sealing tip by relative movement, along an axial direction of the carrier sealing tip, between the carrier sealing tip and a light receiving end of the optical measurement unit.

2. The specimen testing device according to claim 1, wherein the test cartridge container includes: a visible recording medium which displays or can display the specimen information and the test information; and a medium attachment part to which the visible recording medium is attached, and further includes a writing mechanism which automatically writes a measurement result of the optical measurement unit in an empty area of the visible recording medium.

3. The specimen testing device according to claim 2, wherein the writing mechanism comprises a thermal transfer printer mechanism which performs heating and printing to display a digital number.

4. The specimen testing device according to claim 2, wherein the visible recording medium is detachably attached to the medium attaching part of the test cartridge containers.

5. The specimen testing device according to claim 1, wherein the test cartridge containers include one, two or more wells which accommodate in advance one, two or more reagents used to test the specimen, and which are sealed with a pierceable film, and accommodate or can accommodate a piercing tip which is detachably attachable to the nozzle of the dispenser and can pierce the film.

6. The specimen testing device according to claim 1, wherein
the automatic testing unit includes a magnetic member which can apply and remove a magnetic force to and from an inside of the dispenser tip from an outside of the dispenser tip, and
at least one well of the test cartridge containers accommodates a magnetic particle suspension in which magnetic particles are suspended in a liquid.

7. The specimen testing device according to claim 1, wherein the automatic testing unit comprises a temperature controller which can control a temperature in at least one well of the test cartridge containers.

8. The specimen testing device according to claim 7, wherein the automatic testing unit includes: a cap which is openable with respect to an opening part of the well where the temperature is controlled; and a cap-blocked-duration functioning mechanism which uses the suction/discharging mechanism or the moving mechanism to enable the cap to be pressed, shaken or moved when the cap blocks the opening part.

9. The specimen testing device according to claim 7, wherein
the temperature controller includes:
a block which is provided with a translucent well accommodation hole in which the well is accommodated; and
a heating/cooling unit which heats or cools the block, and
the optical measurement unit can optically measure the interior of the well through the well accommodation hole of the block.

10. The specimen testing device according to claim 8, further comprising a light measuring rod which can be moved by the suction/discharging mechanism or a moving mechanism, wherein
the cap has translucency and is provided to fit to a front end of the optical measurement rod; and the optical measurement unit can optically measure an interior of the well through the cap by means of the light measuring rod.

11. The specimen testing device according to claim 7, wherein in the test cartridge containers, a mineral oil or silicon oil is accommodated, and in the well where the temperature is controlled, the mineral oil or the silicon oil is introduced.

12. A specimen testing method comprising:
visibly displaying specimen information for identifying or managing a specimen and test information showing test content, on one, two or more test cartridge containers which comprise a plurality of accommodation parts which accommodate the specimen and one, two or more reagent solutions; a dispenser tip; and a solid-phase built-in tip which is built in a state where an interior of the solid-phase built-in tip can be measured from outside of the solid-phase built-in tip, with the dispenser tip and the solid-phase built-in tip being testing tools used to test the specimen;
producing a predetermined optical state in the interior of the solid-phase built-in tip by causing a reaction of the specimen and the reagent solutions accommodated in the test cartridge containers, using: a dispenser that includes a suction/discharging mechanism which can suck and discharge gas, a nozzle which communicates with the suction/discharging mechanism, and a moving mechanism which is provided with the nozzle relatively movably with respect to the test cartridge containers; and the testing tools which are each detachably attachable to the nozzle;
measuring the optical state of the interior of the solid-phase built-in tip from outside of the solid-phase built-in tip; and
capturing an image of content as one image at one image capturing position, including the specimen information and the test information displayed on the test cartridge containers, by means of a digital camera to obtain image data;
wherein a part of pieces of the specimen and test information is visibly displayed as a code data corresponding to the part of pieces of the specimen and test information on the cartridge containers;
wherein the digital camera includes: an analyzing unit which analyzes whether or not there is code data in the obtained image data, and when the code data is specified, converting the code data into analyzed data matching the code data, to obtain analyzed data; and a data synthesizing unit which synthesizes the image data and the analyzed data to output;
wherein the analyzed data matches the part of pieces of the specimen and test information;
wherein producing the predetermined optical state in the interior of the solid-phase built-in tip comprises: relatively moving the nozzle with respect to the test cartridge containers; attaching the dispenser tip to the nozzle; sucking and discharging a liquid to and from the dispenser tip; attaching the solid-phase built-in tip to the nozzle; and sucking and discharging another liquid to and from the solid-phase built-in tip;
wherein the test information comprises information associated with the solid-phase built-in tip;
wherein the solid-phase built-in tip is a carrier sealing tip having a large diameter tube attachable to the nozzle and a small diameter tube in which carriers of specified fixed positions are sealed in one row, the small diameter tube communicating with the large diameter tube and having a size that allows insertion in one or more of the plurality of accommodation parts;
wherein, with the carriers sealed in the small diameter tube of the carrier sealing tip, chemical substances and the specified fixed positions of the carriers are associated to be measured from outside the carrier sealing tip; and
wherein measuring the optical state of the interior of the solid-phase built-in tip includes measuring the interior of the carrier sealing tip by relative movement, along an axial direction of the carrier sealing tip, between the carrier sealing tip and a light receiving end of an optical measurement unit.

13. A specimen testing device comprising,
a test cartridge container comprising: a first plurality of accommodation parts which accommodate or can accommodate a specimen and one, two or more reagent solutions and a second plurality of accommodation parts which accommodate or can accommodate testing tools used for testing the specimen, wherein the first plurality of accommodation parts which accommodate or can accommodate a specimen and one, two or more reagent solutions are linearly arranged along a longitudinal direction of the test cartridge with the linear arrangement of the first plurality of accommodation parts defining a first length, and wherein the second plurality of accommodation parts which accommodate or can accommodate the testing tools are linearly arranged along the longitudinal direction of the test cartridge container with the linear arrangement of the second plurality of accommodation parts defining a second length; and a seal that extends in the longitudinal direction of the test cartridge container and that is detachably pasted along at least a portion of the first length and at least a portion of the second length such that specimen information for identifying or managing the specimen is visibly displayed along at least a portion of the first length in a first display format and test information showing test content is visibly displayed along at least a portion of the second length in a second display format that is different from the first display format;
an automatic testing unit which is attached with or supports the testing tools and which causes a reaction of the specimen and the reagent solution accommodated in the test cartridge container to obtain a predetermined optical state;

an optical measurement unit which measures the optical state obtained by the automatic testing unit; and a digital camera which captures an image of content as one image at one image capturing position, including the specimen information and the test information displayed on the test cartridge container, to obtain image data;

wherein the digital camera includes: an analyzing unit which analyzes whether or not there is code data in the obtained image data, and when the code data is specified, converting the code data into analyzed data matching the code data, to obtain analyzed data; and a data synthesizing unit which synthesizes the image data and the analyzed data to output;

wherein the analyzed data matches the specimen information and the test information;

wherein the automatic testing unit has a dispenser that includes: a suction/discharging mechanism which can suck and discharge gas; a nozzle which communicates with the suction/discharging mechanism and is detachably attached to the testing tools; and a moving mechanism which is provided with the nozzle relatively movably with respect to the test cartridge container;

wherein the testing tools comprise a dispenser tip and a solid-phase built-in tip which is built in a state where an interior of the solid-phase built-in tip can be measured from outside of the solid-phase built-in tip;

wherein the test cartridge container accommodates or can accommodate the dispenser tip and the solid-phase built-in tip so as to be attached to the nozzle and the optical measurement unit can optically measure an interior of the solid-phase built-in tip from outside the solid-phase built-in tip;

wherein the solid-phase built-in tip is a carrier sealing tip having a large diameter tube attachable to the nozzle and a small diameter tube in which carriers of specified fixed positions are sealed in one row, the small diameter tube communicating with the large diameter tube;

wherein, with the carriers sealed in the small diameter tube of the carrier sealing tip, chemical substances and the specified fixed positions of the carriers are associated to be measured from outside the carrier sealing tip; and wherein the optical measurement unit optically measures the interior of the carrier sealing tip by relative movement, along an axial direction of the carrier sealing tip, between the carrier sealing tip and a light receiving end of the optical measurement unit.

14. A specimen testing method comprising, visibly displaying specimen information for identifying or managing a specimen in a first display format and test information showing test content in a second display format that is different from the first display format, on a test cartridge container comprising: a first plurality of accommodation parts which accommodate the specimen and one, two or more reagent solutions; a dispenser tip; a solid-phase built-in tip which is built in a state where an interior of the solid-phase built-in tip can be measured from outside the solid-phase built-in tip with the dispenser tip and the solid-phase built-in tip being testing tools used to test the specimen; and a second plurality of accommodation parts which accommodate the testing tools;

producing a predetermined optical state in the interior of the solid-phase built-in tip by causing a reaction of the specimen and the reagent solutions accommodated in the test cartridge container, using: a dispenser that includes a suction/discharging mechanism which can suck and discharge gas, a nozzle which communicates with the suction/discharging mechanism, and a moving mechanism which is provided with the nozzle relatively movably with respect to the test cartridge container; and the testing tools which are each detachably attachable to the nozzle;

measuring the optical state of the interior of the solid-phase built-in tip from the outside of the solid-phase built-in tip; and capturing an image of content as one image at one image capturing position, including the specimen information and the test information displayed on the test cartridge container, by means of a digital camera to obtain image data;

wherein the digital camera includes: an analyzing unit which analyzes whether or not there is code data in the obtained image data, and when the code data is specified, converting the code data into analyzed data matching the code data, to obtain analyzed data; and a data synthesizing unit which synthesizes the image data and the analyzed data to output;

wherein the analyzed data matches the specimen information and the test information;

wherein producing the predetermined optical state in interior of the solid-phase built-in tip comprises: relatively moving the nozzle with respect to the test cartridge container; attaching the dispenser tip to the nozzle; attaching the solid-phase built-in tip to the nozzle; sucking and discharging a liquid to and from the dispensing tip; and sucking and discharging another liquid to and from the solid-phase built-in tip;

wherein the first plurality of accommodation parts which accommodate the specimen and the one, two or more reagent solutions are linearly arranged along a longitudinal direction of the test cartridge container, the linear arrangement of the first plurality of accommodation parts defining a first length;

wherein the second plurality of accommodation parts which accommodate the testing tools are linearly arranged along the longitudinal direction of the test cartridge container, the linearly arrangement of the second plurality of accommodation parts defining a second length;

wherein visibly displaying specimen information on the test cartridge container comprises detachably pasting a seal that extends in the longitudinal direction of the test cartridge container and that is detachably pasted along at least a portion of the first length and at least a portion of the second length such that the specimen information is visibly displayed along at least a portion of the first length in the first display format and the test information is visibly displayed along at least a portion of the second length in the second display format that is different from the first display format;

wherein the solid-phase built-in tip is a carrier sealing tip having a large diameter tube attachable to the nozzle and a small diameter tube in which carriers of specified fixed positions are sealed in one row, the small diameter tube communicating with the large diameter tube;

wherein, with the carriers sealed in the small diameter tube of the carrier sealing tip, chemical substances and the specified fixed positions of the carriers are associated to be measured from outside the carrier sealing tip; and wherein measuring the optical state of the interior of the solid-phase built-in tip includes measuring the interior of the carrier sealing tip by relative movement, along an axial direction of the carrier sealing tip, between the carrier sealing tip and a light receiving end of an optical measurement unit.

* * * * *